US010597607B2

(12) United States Patent
Harata et al.

(10) Patent No.: US 10,597,607 B2
(45) Date of Patent: Mar. 24, 2020

(54) METHOD FOR PRODUCING POLYUNSATURATED FATTY ACID-CONTAINING COMPOSITION

(71) Applicant: NISSHIN PHARMA INC., Chiyoda-ku (JP)

(72) Inventors: Masataka Harata, Ueda (JP); Shingo Nonaka, Ueda (JP); Hideki Kanai, Ueda (JP); Hiroyuki Ikemoto, Fujimino (JP); Kenji Takemoto, Fujimino (JP)

(73) Assignee: NISSHIN PHARMA INC., Chiyoda-ku (JP)

( * ) Notice: Subject to any disclaimer, the term of this patent is extended or adjusted under 35 U.S.C. 154(b) by 0 days.

(21) Appl. No.: 16/098,339

(22) PCT Filed: May 1, 2017

(86) PCT No.: PCT/JP2017/017107
§ 371 (c)(1),
(2) Date: Nov. 1, 2018

(87) PCT Pub. No.: WO2017/191821
PCT Pub. Date: Nov. 9, 2017

(65) Prior Publication Data
US 2019/0144780 A1 May 16, 2019

(30) Foreign Application Priority Data

May 2, 2016 (JP) .................................. 2016-092284
Mar. 31, 2017 (JP) .................................. 2017-071002

(51) Int. Cl.
*C11C 1/08* (2006.01)
*C07C 67/48* (2006.01)
(Continued)

(52) U.S. Cl.
CPC ................ *C11C 1/08* (2013.01); *C07C 67/48* (2013.01); *C11B 7/00* (2013.01); *C12M 1/00* (2013.01)

(58) Field of Classification Search
CPC ........................................................ C11C 1/08
(Continued)

(56) References Cited

U.S. PATENT DOCUMENTS 5,189,189 A    2/1993  Misawa et al.
2011/0224452 A1  9/2011  Sakaguchi et al.
(Continued)

FOREIGN PATENT DOCUMENTS

JP    2786748 B2    5/1998
JP    2895258 B2    3/1999
(Continued)

OTHER PUBLICATIONS

Yuri et al.,"Establishnnent of the industrial productionmethod for high-purity DHA ester" DHA Advanced Purification Extraction, p. 1995-96, 1997.*
(Continued)

*Primary Examiner* — Deborah D Carr
(74) *Attorney, Agent, or Firm* — Oblon, McClelland, Maier & Neustadt, L.L.P.

(57) ABSTRACT

Provided is a method for producing a polyunsaturated fatty acid while preventing deterioration of a silver salt solution. A method for producing a composition comprising a polyunsaturated fatty acid, comprising: supplying an aqueous solution comprising a silver salt into a reaction vessel to contact the aqueous solution with a raw material solution comprising an alkyl ester of the polyunsaturated fatty acid; and collecting the aqueous solution comprising the silver salt which has been contacted with the raw material solution from the reaction vessel, wherein the supply of the aqueous
(Continued)

solution comprising the silver salt into the reaction vessel and the collection of the aqueous solution comprising the silver salt from the reaction vessel are carried out concurrently with each other.

29 Claims, 6 Drawing Sheets

(51) Int. Cl.
*C11B 7/00* (2006.01)
*C12M 1/00* (2006.01)

(58) Field of Classification Search
USPC .......................................................... 554/176
See application file for complete search history.

(56) References Cited

U.S. PATENT DOCUMENTS

| | | |
|---|---|---|
| 2015/0252288 A1 | 9/2015 | Harata et al. |
| 2018/0155268 A1 | 6/2018 | Mankura et al. |

FOREIGN PATENT DOCUMENTS

| | | | | |
|---|---|---|---|---|
| JP | 2935555 B2 | | 6/1999 | |
| JP | 3001954 B2 | | 11/1999 | |
| JP | 3001954 B2 | * | 1/2000 | |
| JP | 2015-91940 A | | 5/2015 | |
| JP | 2015091940 A | * | 5/2015 | |
| WO | WO 2010/029706 A1 | | 3/2010 | |
| WO | WO-2010029706 | * | 3/2010 | ............. C07C 67/58 |
| WO | WO 2014/054435 A1 | | 4/2014 | |
| WO | WO-2014054435 | * | 8/2016 | ............... C11C 1/10 |
| WO | WO 2016/194360 A1 | | 12/2016 | |

OTHER PUBLICATIONS

International Search Report dated Jul. 11, 2017 in PCT/JP2017/017107, citing documents AO through AR and AX therein, 2 pages.
Yuri, T., et al., "Establishment of the industrial production method for high-purity DHA ester (examination of the separation and collection of DHA ethyl ester and solvent by silver nitrate method)", DHA advanced purification extraction technology research Kenkyu Hokokusho Heisei 7 to 8 Nendo, 1997, pp. 103-111 with cover pages (with partial English translation).

\* cited by examiner

[Fig.1]
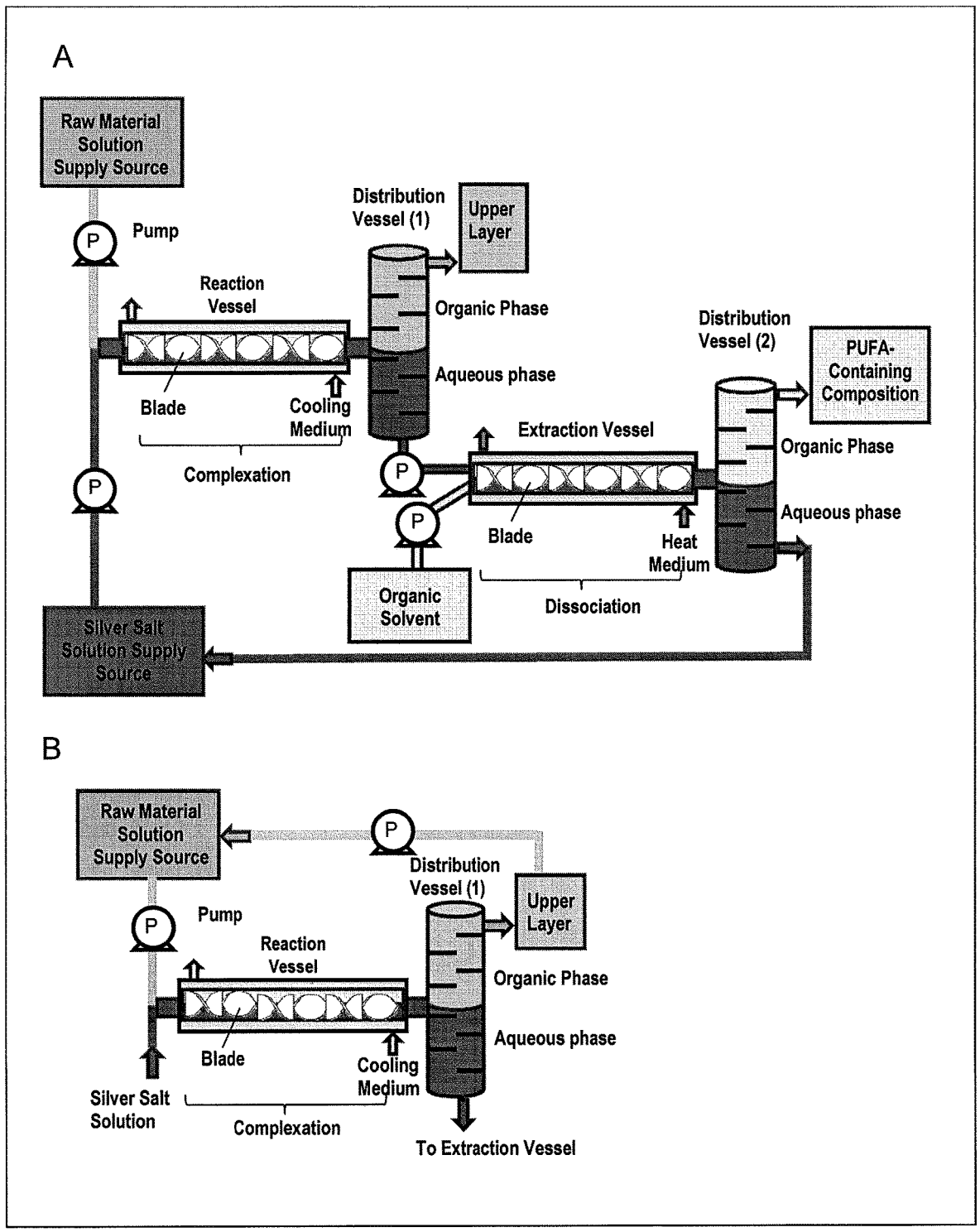

[Fig.2]
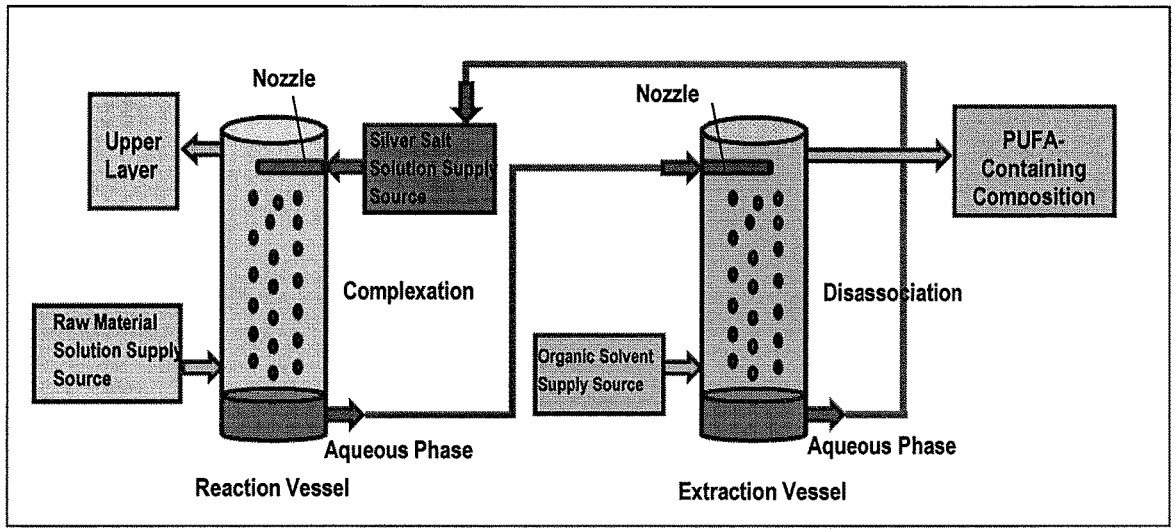
[Fig.3]
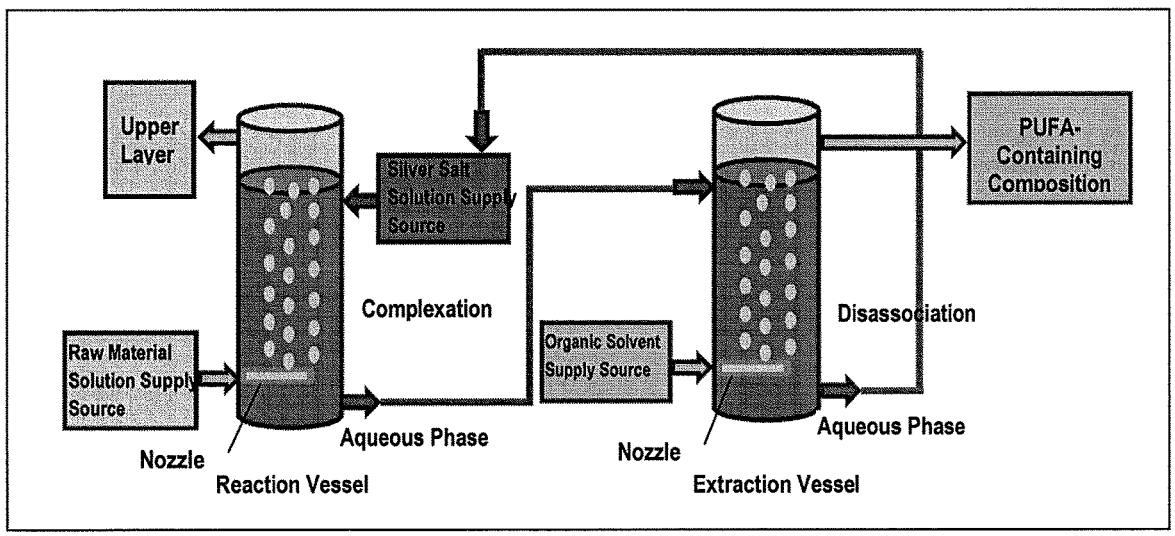

[Fig.4]
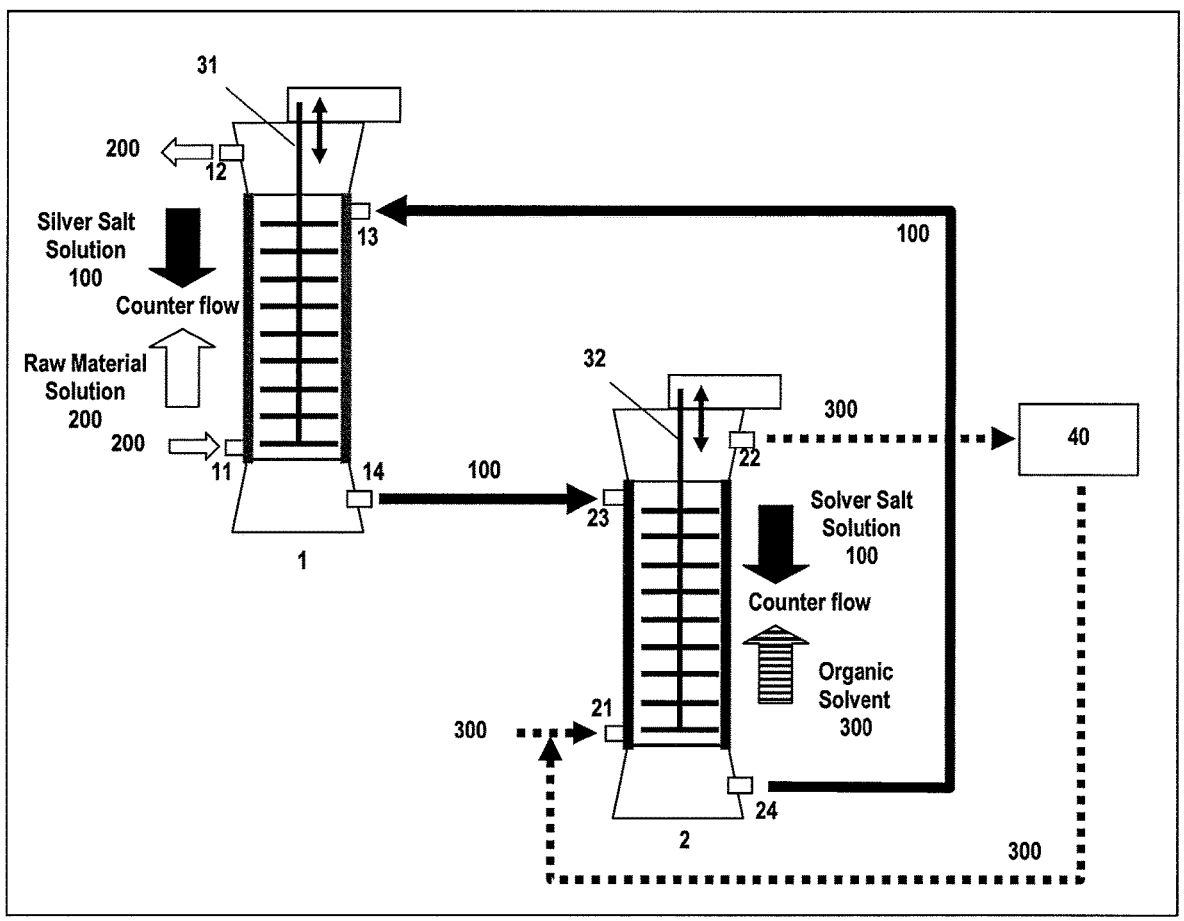

[Fig.6]
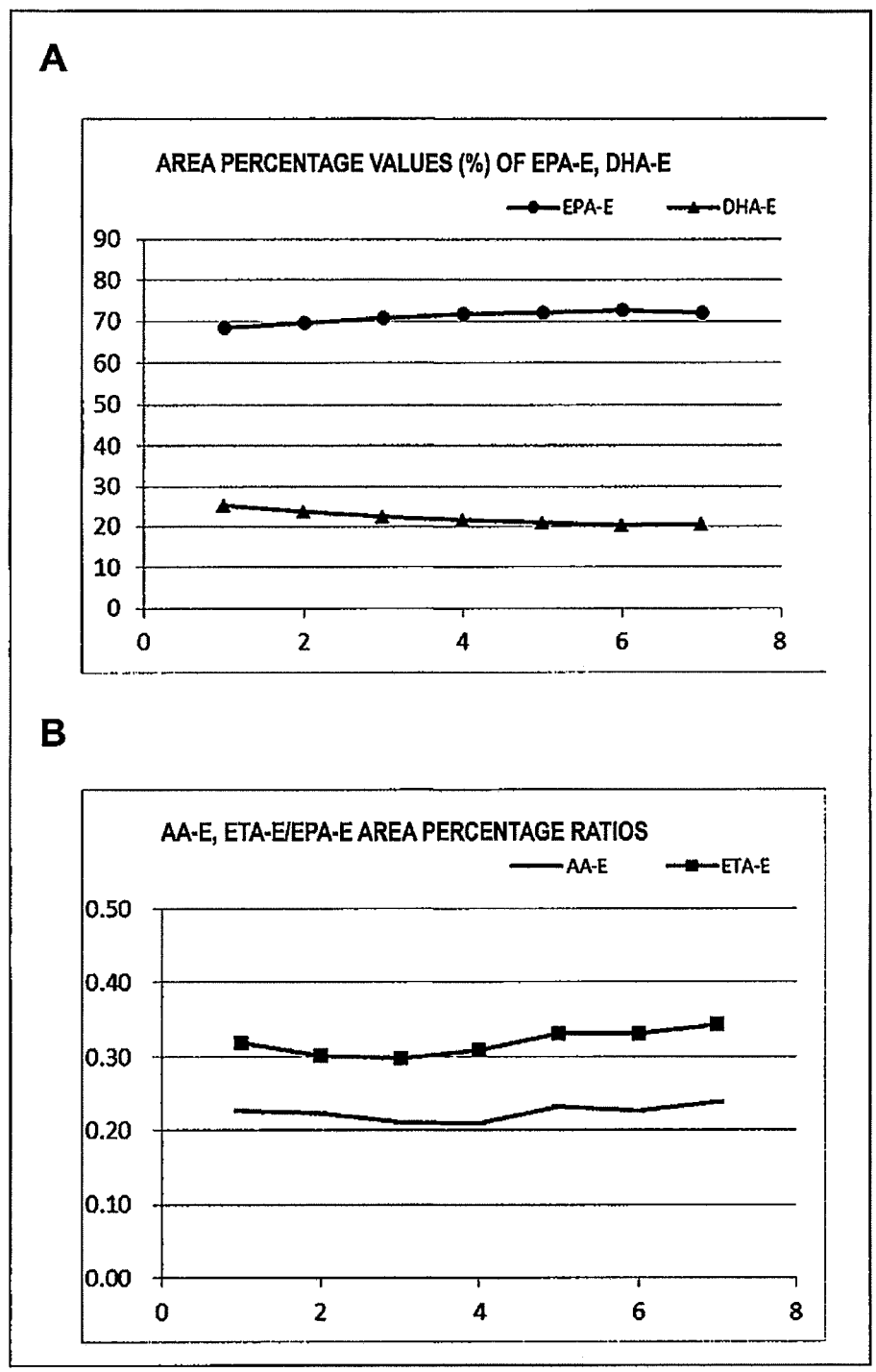

[Fig.7]
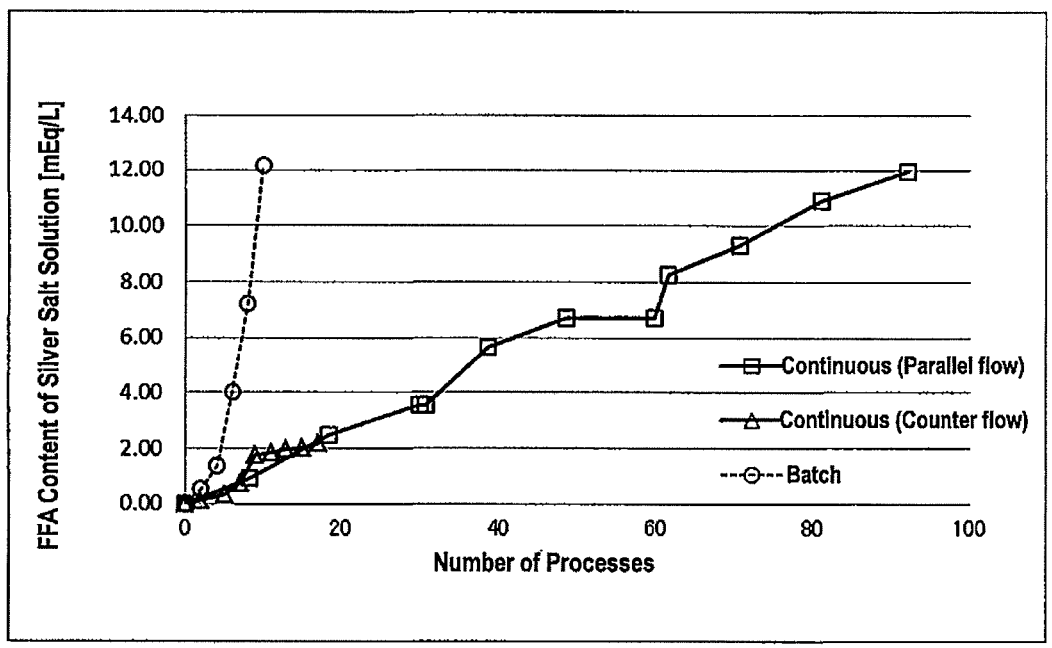

METHOD FOR PRODUCING POLYUNSATURATED FATTY ACID-CONTAINING COMPOSITION

TECHNICAL FIELD

The present invention relates to a method for producing a composition containing a polyunsaturated fatty acid and inhibition of deterioration of a silver salt solution to be used in the production method.

BACKGROUND ART

A polyunsaturated fatty acid (PUFA), such as eicosapentaenoic acid (EPA), docosahexaenoic acid (DHA) and docosapentaenoic acid (DPA), has been revealed for pharmacological effects thereof recently, and has been used as a raw material for drugs and health foods. Production of a PUFA by chemical synthesis is not easy. Therefore, almost all of PUFAs utilized industrially have been produced by extraction or purification from marine organisms-derived PUFA-rich raw materials, e.g., fish oils. However, a biological raw material is a mixture of many types of fatty acids which are different in the number of carbon atoms, the number or position of double bonds, the component ratio of stereoisomers and the like from each other, and therefore a content of a PUFA in the raw material is not always high. For these reasons, it has been demanded to selectively purify a desired PUFA from a biological raw material.

In Patent Literatures 1 to 7, a method is disclosed, in which a raw material containing a PUFA and an aqueous solution containing a silver salt are brought into contact with each other to produce a complex of the PUFA and silver, then the complex is eluted into an aqueous phase, and then the PUFA is extracted from the aqueous phase with an organic solvent. In the method disclosed in Patent Literatures 1 to 7, a PUFA-containing raw material is supplied to a large amount of an aqueous silver salt solution and the resultant solution is preferably stirred to increase the chance of contact between the aqueous solution with the PUFA-containing raw material and therefore promote production of a complex of the PUFA and silver. However, in the above-mentioned conventional method, it is required to use a large-scale facility for producing a PUFA in a large amount, and a batch of an aqueous silver salt solution that has been contacted with a raw material must be collected at every extraction of the PUFA. Therefore, the conventional method is inefficient from the industrial viewpoint. In addition, in the conventional method, there are many chances of contact of the aqueous silver salt solution with oxygen and therefore deterioration of the aqueous silver salt solution may be accelerated. Furthermore, the presence of peroxide contained in a raw material may also deteriorate the aqueous silver salt solution (Patent Literature 7). The deteriorated aqueous silver salt solution is regenerated into silver after collection, and is then re-processed into a silver salt. In this manner, the deteriorated aqueous silver salt solution can be re-used. However, the cost for reproduction of silver and the cost for processing into a silver salt are expensive, and therefore use of a large amount of an aqueous silver salt solution and deterioration of the aqueous silver salt solution may increase the cost of production of a PUFA.

CITATION LIST

Patent Literatures

Patent Literature 1: JP 3001954
Patent Literature 2: JP 2786748
Patent Literature 3: JP 2935555
Patent Literature 4: JP 2895258
Patent Literature 5: JP 2015-091940 A
Patent Literature 6: WO 2014/054435
Patent Literature 7: WO 2016/194360

SUMMARY OF INVENTION

Technical Problem

The present invention relates to a provision of a method by which it becomes possible to produce a PUFA with higher efficiency and lower cost and it also becomes possible to prevent deterioration of a silver salt solution used for the production of a PUFA.

Solution to Problem

The present inventors have found a method for producing a PUFA using an aqueous solution containing a silver salt, in which production of a complex of the PUFA and silver and collection of an aqueous phase containing the complex are carried out continuously by carrying out supply of the silver salt solution into a reaction vessel and collection of the silver salt solution that has been contacted with a raw material oil or fat from the reaction vessel concurrently with each other.

The present inventors also have found that, in a purification of a PUFA using an aqueous solution containing a silver salt, production of a complex of the PUFA and a silver salt and collection of an aqueous phase containing the complex can be carried out continuously by supplying an aqueous solution containing the silver salt from above a raw material containing the PUFA and falling the aqueous solution downward in the raw material to be contacted with the raw material, and then collecting the aqueous solution.

The present inventors also have found that, according to the method, deterioration of an aqueous solution containing a silver salt during production of the PUFA can be prevented. The present inventors also have found that, according to the method, the amount of the aqueous solution containing the silver salt to be used can be reduced.

Therefore, the present invention provides a method for producing a composition comprising a polyunsaturated fatty acid, comprising:

supplying an aqueous solution comprising a silver salt into a reaction vessel to be contacted with a raw material solution comprising an alkyl ester of the polyunsaturated fatty acid; and collecting the aqueous solution comprising the silver salt which has been contacted with the raw material solution from the reaction vessel, wherein the supply of the aqueous solution comprising the silver salt into the reaction vessel and the collection of the aqueous solution comprising the silver salt from the reaction vessel are carried out concurrently with each other.

Furthermore, the present invention provides a method for producing a composition comprising a polyunsaturated fatty acid, comprising:

supplying an aqueous solution comprising a silver salt into a raw material solution comprising an alkyl ester of the polyunsaturated fatty acid to fall the aqueous solution comprising the silver salt downward in the raw material solution, thereby contacting the aqueous solution comprising the silver salt with the raw material solution; and collecting the aqueous solution which has been contacted with the raw material solution, wherein the temperature of the aqueous solution that is to be contacted with the raw material solution is from 5 to 30° C., and the supply of the aqueous solution and the collection of the aqueous solution are carried out concurrently with each other.

Furthermore, the present invention provides an apparatus for producing a composition comprising a polyunsaturated fatty acid comprising a first reaction vessel, wherein the first reaction vessel comprises a raw material solution inlet port through which a raw material solution comprising an alkyl ester of the polyunsaturated fatty acid is to be supplied into the reaction vessel, an aqueous solution inlet port through which a aqueous solution comprising a silver salt is to be supplied into the reaction vessel, an aqueous solution collection port through which the aqueous solution that has been contacted with the raw material solution is to be collected, and a raw material solution collection port through which the raw material solution that has been contacted with the aqueous solution is to be collected, the raw material solution inlet port is arranged at the lower part of the first reaction vessel and above the aqueous solution collection port, the aqueous solution inlet port is arranged at the upper part of the first reaction vessel, above the raw material solution inlet port and below the raw material solution collection port, and the aqueous solution comprising the silver salt which has been supplied through the aqueous solution inlet port flows downward in the first reaction vessel and the raw material solution which has been supplied through the raw material inlet port flows upward in the first reaction vessel while flowing countercurrently to each other in the reaction vessel so that the aqueous solution and the raw material solution can contact with each other, and the contacted aqueous solution is collected outside the reaction vessel through the aqueous solution collection port.

BRIEF DESCRIPTION OF DRAWINGS

FIG. 1A illustrates a schematic diagram of an example of a parallel-flow-mode apparatus for producing a PUFA-containing composition.

FIG. 1B illustrates a partial schematic diagram of an apparatus equipped with a pathway through which a raw material solution collected from a distribution vessel (1) is returned to a reaction vessel.

FIG. 2 illustrates a schematic diagram of an example of a counter-flow-mode apparatus for producing a PUFA-containing composition using a silver salt solution as a dispersed phase.

FIG. 3 illustrates a schematic diagram of an example of a counter-flow-mode apparatus for producing a PUFA-containing composition using a silver salt solution as a continuous phase.

FIG. 4 illustrates one embodiment of a counter-flow-mode apparatus for producing a PUFA-containing composition.

FIG. 6 illustrates a change in the fatty acid composition in a composition containing a polyunsaturated fatty acid with repeated use of an aqueous silver salt solution, A: area percentage values (%) of EPA-E and DHA-E, B: AA-E/EPA-E area percentage ratio and the ETA-E/EPA-E area percentage ratio, horizontal axis: the number of repeats.

FIG. 7 illustrates the change over time in free fatty acid content with the repeated use of a silver salt solution.

DESCRIPTION OF EMBODIMENTS

Figure 5A:
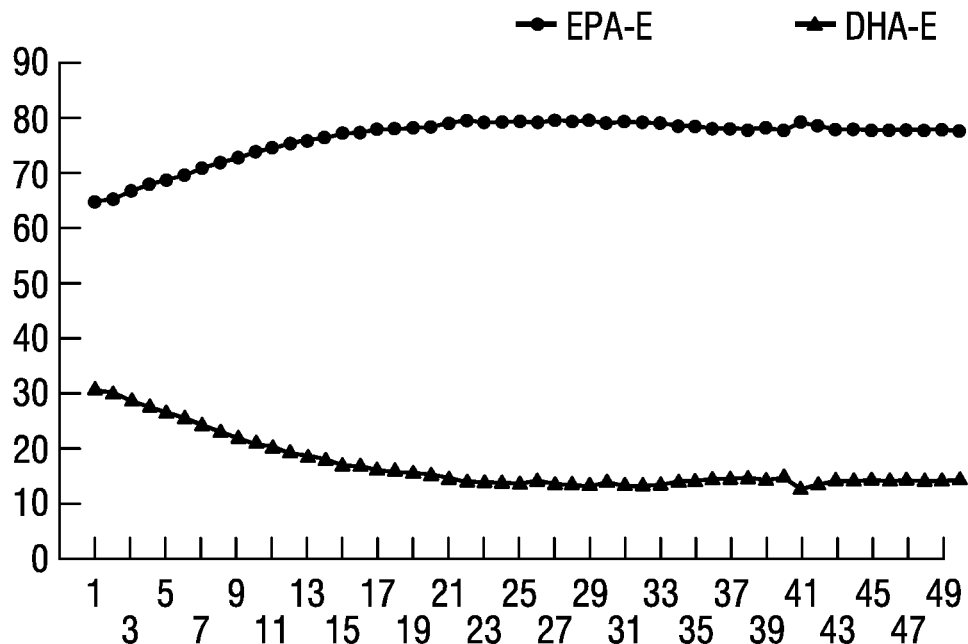
FIG. 5 illustrates a change in the fatty acid composition in a composition containing a polyunsaturated fatty acid with repeated use of a silver salt solution. A: area percentage values (%) of EPA-E and DHA-E, B: AA-E/EPA-E area percentage ratio and the ETA-E/EPA-E area percentage ratio, horizontal axis: the number of repeats.

The exemplary embodiments of the present invention are disclosed in the followings.

[1] A method for producing a composition comprising a polyunsaturated fatty acid, comprising:

supplying an aqueous solution comprising a silver salt into a reaction vessel to contact the aqueous solution with a raw material solution comprising an alkyl ester of the polyunsaturated fatty acid; and collecting the aqueous solution comprising the silver salt which has been contacted with the raw material solution from the reaction vessel, wherein the supply of the aqueous solution comprising the silver salt into the reaction vessel and the collection of the aqueous solution comprising the silver salt from the reaction vessel are carried out concurrently with each other.

[2] The method according to [1], wherein the supply of the aqueous solution comprising the silver salt into the reaction vessel, the contact of the aqueous solution comprising the silver salt with the raw material solution, and the collection of the aqueous solution comprising a silver salt from the reaction vessel are carried out under a low oxygen condition.

[3] The method according to [1] or [2], wherein the raw material solution comprising an alkyl ester of the polyunsaturated fatty acid has such an oxidation index that a POV is 10 or less or an AV is 0.3 or less.

[4] The method according to any one of [1] to [3], wherein the polyunsaturated fatty acid comprises eicosapentaenoic acid or docosahexaenoic acid.

[5] The method according to any one of [1] to [4], wherein in the reaction vessel, the aqueous solution comprising the silver salt exists in a form of a dispersed phase and the raw material comprising an alkyl ester of the polyunsaturated fatty acid exists in a form of a continuous phase, or the aqueous solution comprising the silver salt exists in a form of a continuous phase and the raw material comprising an alkyl ester of the polyunsaturated fatty acid exists in a form of a dispersed phase.

[6] The method according to any one of [1] to [5], further comprising:

supplying the aqueous solution comprising a silver salt which has been collected from the reaction vessel into an extraction vessel to be contacted with an organic solvent; and collecting the contacted aqueous solution comprising the silver salt from the extraction vessel, wherein the supply of the aqueous solution comprising the silver salt into the extraction vessel and the collection of the aqueous solution comprising the silver salt from the extraction vessel are carried out concurrently with each other.

[7] The method according to [6], further comprising supplying the aqueous solution comprising the silver salt which is collected from the extraction vessel into the reaction vessel again.

[8] The method according to [6] or [7], wherein the supply of the aqueous solution comprising the silver salt into the extraction vessel, the contact of the aqueous solution comprising the silver salt with the organic solvent and the collection of the aqueous solution comprising the silver salt from the extraction vessel are carried out under a low oxygen condition.

[9] The method according to any one of [6] to [8], wherein in the extraction vessel, the aqueous solution comprising the silver salt exists in a form of a dispersed phase and the organic solvent exists in a form of a continuous phase, or the aqueous solution comprising the silver salt exists in a form of a continuous phase and the organic solvent exists in a form of a dispersed phase.

[10] The method according to any one of [6] to [9], wherein the organic solvent is hexane or cyclohexane.

[11] A method for producing a composition comprising a polyunsaturated fatty acid, comprising:

supplying an aqueous solution comprising a silver salt into a raw material solution comprising an alkyl ester of polyunsaturated fatty acid to fall the aqueous solution comprising the silver salt downward in the raw material solution, thereby contacting the aqueous solution comprising the silver salt with the raw material solution; and collecting the aqueous solution that has been contacted with the raw material solution, wherein the temperature of the aqueous solution that is to be contacted with the raw material solution is from 5 to 30° C., and the supply of the aqueous solution and the collection of the aqueous solution are carried out concurrently with each other.

[12] The method according to [11], wherein the contact of the aqueous solution comprising the silver salt with the raw material solution comprising an alkyl ester of polyunsaturated fatty acid comprises supplying the aqueous solution from an upper part of a first reaction vessel and supplying the raw material solution from a lower part of the first reaction vessel while flowing countercurrently to each other in the first reaction vessel to contact the aqueous solution and the raw material solution with each other, and the collection of the aqueous solution comprises collecting the aqueous solution that has been contacted with the raw material solution from a part located below an inlet port for the raw material solution in the first reaction vessel.

[13] The method according to [11] or [12] further comprising:

supplying the collected aqueous solution into an organic solvent to fall the aqueous solution downward in the organic solvent, thereby contacting the aqueous solution with the organic solvent; and collecting the organic solvent that has been contacted with the aqueous solution, wherein the temperature of the aqueous solution to be contacted with the organic solvent is from 30 to 80° C., and the supply of the aqueous solution and the collection of the organic solvent are carried out concurrently with each other.

[14] The method according to [13], wherein the contact of the aqueous solution with the organic solvent comprises supplying the collected aqueous solution from an upper part of a second reaction vessel and supplying the organic solvent from a lower part of the second reaction vessel while flowing countercurrently to each other in the second reaction vessel to contact the aqueous solution with the organic solvent each other, and the collection of the organic solvent comprises collecting the organic solvent that has been contacted with the aqueous solution from a part located above an inlet port for the aqueous solution in the second reaction vessel.

[15] The method according to [13], further comprising collecting the aqueous solution that has been contacted with the organic solvent.

[16] The method according to [14], further comprising collecting the aqueous solution that has been contacted with the organic solvent from a part located below an inlet port for the organic solvent in the second reaction vessel.

[17] The method according to claim 15, wherein the aqueous solution comprising a silver salt which is to be supplied into the raw material solution comprising an alkyl ester of polyunsaturated fatty acid comprises the aqueous solution that is collected after contacting the aqueous solution with the organic solvent.

[18] The method according to [16], wherein the aqueous solution to be supplied into the first reaction vessel includes an aqueous solution collected from the second reaction vessel

[19] The method according to anyone of [12] to [18], wherein the first reaction vessel is a closed system.

[20] The method according to anyone of [14] to [19], wherein the second reaction vessel is a closed system.

[21] The method according to anyone of [11] to [20], wherein the aqueous solution forms a dispersed phase and the raw material comprising the alkyl ester of polyunsaturated fatty acid forms a continuous phase.

[22] The method according to anyone of [13] to [21], wherein the aqueous solution forms a dispersed phase and the organic solvent forms a continuous phase.

[23] The method according to [21] or [22], wherein the dispersed phase is in a form of liquid droplets or mists.

[24] The method according to any one of [11] to [23], wherein the polyunsaturated fatty acid comprises eicosapentaenoic acid or docosahexaenoic acid.

[25] The method according to any one of [11] to [24], wherein, the concentration of the silver salt in the aqueous solution comprising the silver salt is 30% by mass or more.

[26] The method according to any one of [11] to [25], wherein the organic solvent is at least one organic solvent selected from hexane and cyclohexane.

[27] An apparatus for producing a composition comprising a polyunsaturated fatty acid comprising a first reaction vessel, wherein the first reaction vessel comprises a raw material solution inlet port through which a raw material solution comprising an alkyl ester of the polyunsaturated fatty acid is to be supplied into the reaction vessel, an aqueous solution inlet port through which an aqueous solution comprising a silver salt is to be supplied into the reaction vessel, an aqueous solution collection port through which the aqueous solution that has been contacted with the raw material solution is to be collected, and a raw material solution collection port through which the raw material solution that has been contacted with the aqueous solution is to be collected, the raw material solution inlet port is arranged at the lower part of the first reaction vessel and above the aqueous solution collection port, the aqueous solution inlet port is arranged at the upper part of the first reaction vessel, above the raw material solution inlet port and below the raw material solution collection port, and the aqueous solution comprising the silver salt which has been supplied through the aqueous solution inlet port flows downward in the first reaction vessel and the raw material solution which has been supplied through the raw material inlet port flows upward in the first reaction vessel while flowing countercurrently to each other in the first reaction vessel so that the aqueous solution and the raw material solution are contacted with each other, and the contacted aqueous solution is collected outside the reaction vessel through the aqueous solution collection port.

[28] The apparatus according to [27],
further comprising a second reaction vessel,
wherein the second reaction vessel comprises an organic solvent inlet port through which an organic solvent is to be supplied into the reaction vessel, n aqueous solution inlet port through which the aqueous solution collected through the aqueous solution collection port in the first reaction vessel is to be supplied into the second reaction vessel, an aqueous solution collection port through which the aqueous solution that has been contacted with the organic solvent is to be collected, and an organic solvent collection port through which the organic solvent that has been contacted with the aqueous solution is to be collected,
the organic solvent inlet port is arranged at the lower part of the second reaction vessel and above the aqueous solution collection port,
the aqueous solution inlet port is arranged at the upper part of the second reaction vessel, above the organic solvent inlet port and below the organic solvent collection port, and
the aqueous solution supplied through the aqueous solution inlet port flows downward in the second reaction vessel whereas the organic solvent supplied through the organic solvent inlet port flows upward in the second reaction vessel while flowing countercurrently to each other in the second reaction vessel so that the aqueous solution and the organic solvent are contacted with each other, and the contacted aqueous solution is collected outside the second reaction vessel through the aqueous solution collection port.

[29] The apparatus according to [28], wherein the aqueous solution collected from the second reaction vessel is supplied into the first reaction vessel through the aqueous solution inlet port in the first reaction vessel.

[30] The apparatus according to any one of [27] to [29], wherein the first or second reaction vessel comprises a temperature controller for controlling the temperature of the aqueous solution in the reaction vessel.

[31] The apparatus according to any one of [27] to [30], wherein the first or second reaction vessel comprises a liquid distributor for converting the aqueous solution to be supplied through the aqueous solution inlet port into a dispersed phase.

[32] The method according to anyone of [11] to [26], wherein the method is carried out using the apparatus according to [27] to [31].

The term "polyunsaturated fatty acid (PUFA)" as used herein refers to a fatty acid having at least two unsaturated bonds. Examples of the PUFA include linoleic acid (LA, 18:2n-6), γ-linolenic acid (GLA, 18:3n-6), arachidonic acid (AA, 20:4n-6), α-linolenic acid (ALA, 18:3n-3), eicosatetraenoic acid (ETA, 20:4n-3), docosapentaenoic acid (DPA, 22:5n-3), eicosapentaenoic acid (EPA, 20:5n-3) and docosahexaenoic acid (DHA, 22:6n-3). In the method for producing the PUFA-containing composition according to the present invention, the PUFA to be contained in the produced composition is preferably at least one compound selected from the group consisting of EPA, DHA and DPA, more preferably at least one compound selected from the group consisting of EPA and DHA, still more preferably EPA.

In the method according to the present invention, a PUFA alkyl ester is separated and purified utilizing the fact that the solubility of a PUFA in an extraction solvent varies when a silver salt forms a complex at a double bond part in the PUFA. In the method according to the present invention, an alkyl ester of EPA, AA, ETA, DHA or DPA which has 20 or more carbon atoms can be separated and purified with high efficiency.

A major example of the raw material for the PUFA-containing composition which can be used in the present invention is a natural product-derived oil or fat mixture which contains the above-mentioned PUFA. Specific examples of the raw material include: an oil or fat derived from a marine animal, for example, fish, or a plankton; and an oil or fat derived from a microorganism, e.g., an alga. Among these oils or fats, an oil or fat derived from a fish such as sardine and yellowtail and an oil or fat derived from an alga are preferred.

The raw material for the PUFA-containing composition to be used in the present invention is preferably an oil or fat that contains a desired PUFA (preferably at least one compound selected from the group consisting of EPA, DHA and DPA, more preferably at least one compound selected from the group consisting of EPA and DHA, still more preferably EPA) in an amount of 15% by mass or more, more preferably 40% by mass or more, relative to the whole mass of the contained fatty acid (s). The raw material preferably contains EPA, DHA and DPA at a large total content as possible. From the viewpoint of cost and availability, the total content of EPA, DHA and DPA in the raw material is preferably 65% by mass or less, more preferably 60% by mass or less, still more preferably 55% by mass or less, in the total fatty acids contained. The PUFA in the raw material may be present in a form of a free fatty acid or in a form of a fatty acid chain such as a mono-, di- or tri-glyceride.

In the method according to the present invention, the PUFA in the raw material is alkyl-esterified. It is preferred that the raw material contains an alkyl ester of a desired PUFA (preferably at least one compound selected from the group consisting of EPA, DHA and DPA, more preferably at least one compound selected from the group consisting of EPA and DHA, still more preferably EPA). An example of the alkyl group that constitutes the alkyl ester of the PUFA is a linear or branched alkyl group having 1 to 6 carbon atoms, preferably a methyl group or an ethyl group, more preferably an ethyl group. A higher degree of alkyl esterification is preferred, and it is preferred that 80% or more, more preferably 90% or more, of the whole amount of the desired PUFA (including a free form thereof) contained in the raw material is alkyl-esterified.

The raw material containing the alkyl ester of the PUFA can be produced by subjecting an oil or fat containing the PUFA and an acid having a desired alkyl group to an esterification reaction by a known method. For example, an alkyl-esterification product of a PUFA can be produced easily by subjecting an oil or fat containing a triglyceride of the PUFA to a saponification treatment. Alternatively, as a raw material containing the alkyl ester of the PUFA, a commercially available oil or fat may be used. For example, a commercially available fish-oil-derived oil or fat in which the type and amount of a PUFA contained therein are standardized can be used preferably.

From the viewpoint of quality preservation of the PUFA-containing composition to be produced in the present invention andprevention of deterioration of the aqueous solution containing a silver salt, it is preferred that the raw material containing the alkyl ester of the PUFA to be used in the present invention has a small oxidation index. An oxidation index of a lipid can be expressed in, for example, a peroxide value (POV) or an acid value (AV). The raw material containing the alkyl ester of the PUFA to be used in the present invention preferably has a POV (mEq/kg) of 10 or less, more preferably 5 or less, or preferably has an AV (mg/g) of 0.3 or less, more preferably 0.2 or less. It is still more preferred that the raw material containing the alkyl ester of the PUFA to be used in the present invention has a POV of 10 or less and an AV of 0.3 or less, more preferably a POV of 5 or less and an AV of 0.2 or less. A POV can be measured by, for example, an iodine titration method (ISO 3960:2007). An AV can be measured by, for example, a potassium hydroxide titration method (ISO 660:2009).

In the method according to the present invention, the above-mentioned raw material containing the alkyl ester of the PUFA in a form of a liquid (a raw material solution) is brought into contact with the aqueous solution containing a silver salt (which is also referred to as a "silver salt solution" or simply referred to as an "aqueous solution" in the description). For the purpose of keeping the liquid state at a temperature upon contact with the silver salt solution, the raw material may be dissolved in or diluted with an organic solvent or another oil, if necessary. Examples of the organic solvent include ethyl acetate, chloroform, carbon tetrachloride, diethyl ether, hexane and cyclohexane.

The silver salt contained in the silver salt solution to be used in the method according to the present invention is not particularly limited, as long as the silver salt can form a complex with the unsaturated bond in a PUFA. Examples of the silver salt include silver nitrate, silver perchlorate, silver tetrafluoroborate and silver acetate. Among these compounds, silver nitrate is preferred. A solvent for the silver salt solution may be water or a solvent mixture of water and a compound having a hydroxyl group, e.g., glycerin or ethylene glycol. Water is used preferably. The concentration of the silver salt in the silver salt solution may be 20% by mass or more, preferably is 30% by mass or more. In a preferred embodiment, the concentration of the silver salt in the silver salt solution is from 20 to 80% by mass, preferably from 30 to 70% by mass.

(1. Method for Producing PUFA-containing Composition)

The method for producing a composition containing a polyunsaturated fatty acid according to the present invention includes:

supplying an aqueous solution containing a silver salt into a reaction vessel to be contacted with a raw material solution containing an alkyl ester of the polyunsaturated fatty acid; and collecting the aqueous solution containing the silver salt which has been contacted with the raw material solution from the reaction vessel. In the method, the supply of the aqueous solution containing a silver salt into the reaction vessel and the collection of the aqueous solution containing a silver salt from the reaction vessel are carried out concurrently with each other.

In the method for producing the PUFA-containing composition according to the present invention, addition of the silver salt solution to the raw material oil or fat and collection of the silver salt solution which has been reacted with the raw material oil or fat are carried out concurrently and continuously. In the method according to the present invention, unlike the conventional batch-mode PUFA production methods, an operation for collecting the silver salt solution in every PUFA collection process is not needed. According to the method of the present invention, the amount of the silver salt solution used can be reduced and deterioration of the silver salt solution can be prevented. Therefore, according to the present invention, both of reduction in size of the facility used in the PUFA production and reduction in cost can be achieved.

(1-1. Production of Complex)

In the method according to the present invention, when the raw material solution is contacted with the silver salt solution, a complex of the PUFA and silver (which is also referred to as a "PUFA-silver complex" in the description) is formed. The formed complex moves into an aqueous phase, that is, a phase of the silver salt solution. Therefore, a solution containing the PUFA-silver complex can be obtained by collecting the silver salt solution that has been contacted with the raw material solution.

In the method according to the present invention, the contact of the raw material solution with the silver salt solution is mostly carried out in a first reaction vessel (where the PUFA and the silver salt contact with each other, hereinafter also referred to as a "reaction vessel" simply) for forming the PUFA-silver complex. In the method according to the present invention, the silver salt solution is supplied into the reaction vessel to be contacted with the raw material solution containing the alkyl ester of the PUPA in the reaction vessel.

The temperature of the silver salt solution upon contact with the raw material solution is preferably from 5 to 30° C., more preferably from 15 to 30° C. Examples of a method for keeping the temperature of the silver salt solution within the above-mentioned range upon contact with the raw material solution, include a method in which the raw material solution and/or the silver salt solution is warmed or cooled to a temperature falling within the above-mentioned range and then these solution are contacted with each other, a method in which the temperature of the reaction vessel for contact of the raw material solution and the silver salt solution is kept within the above-mentioned range, and a combination of these methods.

In the method according to the present invention, the supply of the silver salt solution into the reaction vessel, the contact thereof with the raw material solution, and the collection of the complex-containing silver salt solution which has been contacted with the raw material solution from the reaction vessel are carried out concurrently with one another. Therefore, in the method according to the present invention, unlike the conventional batch-mode methods, it is not needed to replace the whole of the silver salt solution in the reaction vessel by a fresh one after the complex-producing reaction, and the collection of the complex-containing silver salt solution can be continued while continuing the supply of the silver salt solution to the raw material solution and the contact with the raw material solution. In other words, in the method according to the present invention, the contact of the raw material solution with the silver salt solution and the collection of the complex-containing silver salt solution can be carried out continuously (that is, in a continuous mode).

In the method according to the present invention, the raw material solution containing the alkyl ester of the PUFA can be supplied into the reaction vessel continuously or intermittently. In the method according to the present invention, it is preferred that the supply of the raw material solution into the reaction vessel and the collection of the raw material solution that has been contacted with the silver salt solution are carried out concurrently with each other. It is more preferred that a process of supplying the raw material solution and collecting the raw material solution is carried out in a continuous mode and concurrently with the above-mentioned process of supplying the silver salt solution and collecting the silver salt solution. Alternatively, in the method according to the present invention, a portion or the whole of the raw material solution in the reaction vessel may be replaced by a fresh one at regular time intervals. For example, the reaction vessel is filled with the raw material solution in advance and then a process of supplying, into and collecting from the reaction vessel, of the silver salt solution may be carried out for a certain time period. Furthermore, the filling or replacement of the raw material solution in the reaction vessel and the process of supplying, into and collecting from the reaction vessel, of the silver salt solution may be repeated one after the other.

The supply of the silver salt solution and the raw material solution into the reaction vessel is preferably carried out through a flow path that is fluid-communicated with the reaction vessel (the flow path is hereinafter also referred to as a "supply passage"). These supply passages are provided separately for supplying the silver salt solution and supplying the raw material solution and establish fluid-communication of a supply source for the silver salt solution and a supply source for the raw material solution with the reaction vessel, respectively. Each of the supply passages may be provided with, for example, a valve, a pump, and a valve. Each of the supply passages may be connected to the reaction vessel directly, or the supply passages may be connected to each other collectively and then connected to the reaction vessel.

Each of the silver salt solution and the raw material solution supplied to the reaction vessel may form a continuous phase or a dispersed phase in the reaction vessel. In one embodiment, the raw material solution exists in a form of a continuous phase and the silver salt solution exists in a form of a dispersed phase in reaction vessel. In this case, the dispersed phase of the silver salt solution may preferably be in a form of liquid droplets dispersed in the continuous phase of the raw material solution. In another embodiment, the raw material solution exists in a form of a dispersed phase and the silver salt solution exists in a form of a continuous phase in the reaction vessel. In this case, the dispersed phase of the raw material solution may be preferably in a form of liquid droplets dispersed in the continuous phase of the silver salt solution. In formation of the dispersed phase of the silver salt solution or the raw material solution, any method capable of dispersing a liquid may be employed. For example, in the case where the raw material solution is in a form of a continuous phase and the silver salt solution is in a form of a dispersed phase, a method of adding the silver salt solution dropwise to the reaction vessel filled with the raw material solution (continuous phase) or spraying the silver salt solution through a nozzle or the like, a method of stirring the solution in the reaction vessel using, for example, a vibrator or a stirring machine to make the silver salt solution more fine, and a method of passing the silver salt solution through, for example, a liquid distributor or a porous dispersion board to make the silver salt solution more fine may be used. The same can apply to the case where the raw material solution is formed into a dispersed phase.

Alternatively, both of the silver salt solution and the raw material solution may exist in a form of continuous phases in the reaction vessel. In one embodiment, the silver salt solution in the reaction vessel runs through the continuous phase of the raw material solution. In another embodiment, each liquid flow of the silver salt solution and the raw material solution exists in the reaction vessel and the liquid flows may be countercurrent or parallel, and in contact with each other.

The silver salt solution supplied to the reaction vessel can contact with the raw materials solution while moving in the reaction vessel so as to contain a produced PUFA-silver complex, regardless of the form of the silver salt solution, that is, a continuous phase or a dispersed phase. In one embodiment, the complex-containing silver salt solution flows out from the reaction vessel together with the raw material solution. In another embodiment, the complex-containing silver salt solution is accumulated in the bottom part of the reaction vessel to form a continuous aqueous phase, and the continuous aqueous phase is collected from the reaction vessel.

The direction of movement of the silver salt solution in the reaction vessel is affected by an operation such as the ejection, vibration and stirring of the silver salt solution, and can be roughly determined by the arrangement of an inlet port and a collection port for the silver salt solution in the reaction vessel.

The formation of a complex of the PUFA and silver can be accelerated by increasing the contact frequency of the silver salt solution with the raw material solution in the reaction vessel. The contact frequency can be controlled by changing, for example, the capacity of the reaction vessel, the volume ratio between the raw material solution and the silver salt solution in the reaction vessel, the flow amount or flow rate of the silver salt solution or the raw material solution to be supplied to and collected from the reaction vessel, the size (e.g., a liquid droplet diameter) of the dispersed phase of the silver salt solution or the raw material solution. In a preferred embodiment, the size of the reaction vessel is as follows: the volume is about from 1 cm$^3$ to 10 m$^3$ and the distance between the inlet port and the collection port for the silver salt solution or the raw material solution in the reaction vessel is about from 15 to 400 cm. It is preferred that the flow amount of the silver salt solution to be supplied to and collected from the reaction vessel is about from 100 to 5000 g/sec. It is preferred that the volume ratio between the silver salt solution and the raw material solution which flow in the reaction vessel is adjusted to about 1:0.25 to 1. It is preferred that either of the silver salt solution or the raw material solution forms a dispersed phase, and the other forms a continuous phase in the reaction vessel. Regardless of which forms a dispersed phase, it is preferred that the dispersed phase in the reaction vessel is prepared in a form of liquid droplets each having a particle diameter (a 50% particle diameter; same applies in the description) of about 0.05 to 5 mm. The retention time of each of the raw material solution and the silver salt solution in the reaction vessel is preferably about from 1 to 300 seconds regardless of the form, a dispersed phase or a continuous phase.

It is preferred that the collection of the silver salt solution and the raw material solution from the reaction vessel is carried out through flow paths that are in fluid-communication with the reaction vessel (hereinafter also referred to as "collection passages"). The collection passages are arranged separately for collecting the silver salt solution and collecting the raw material solution. Each of the collection passages may be provided with, for example, a valve, a pump, and a valve. Each of the collection passages may be connected to the reaction vessel directly, or may be connected to a distribution vessel or the like as mentioned below which is connected to the reaction vessel.

In the case where the complex-containing silver salt solution flows out together with the raw material solution from the reaction vessel, the silver salt solution is fractionated from a liquid flowing out. It is preferred that the liquid flowing out from the reaction vessel and containing both of the raw material solution and the silver salt solution is transferred to the distribution vessel and the liquid is distributed into a phase of the raw material solution (an organic phase) and a phase of the silver salt solution (an aqueous phase). When the distributed aqueous phase is fractionated, the complex-containing silver salt solution can be collected. When the distributed organic phase is fractionated, the used raw material solution can be collected. The collection of the silver salt solution and the collection of the raw material solution from the distribution vessel can be achieved respectively through collection passages connected to the distribution vessel. In order to facilitate the collection of the organic phase and the aqueous phase thus distributed, it is preferred that an outlet port for the silver salt solution from the distribution vessel is arranged on a bottom surface or a lower wall surface of the distribution vessel, and an outlet port for the raw material solution is arranged on an top surface or an upper wall surface of the distribution vessel. It is also preferred that the silver salt solution is sucked through a nozzle arranged at a lower part, preferably on bottom surface, in the distribution vessel to be collected from the distribution vessel.

In the case where a continuous aqueous phase of the complex-containing silver salt solution collected in the reaction vessel is collected, the silver salt solution collection passage is connected directly to the reaction vessel, and the silver salt solution is collected therethrough. It is also possible to connect a raw material solution collection passage to the reaction vessel and collect the raw material solution therethrough. It is preferred that the silver salt solution collection passage is arranged on a bottom surface or a lower wall surface of the reaction vessel and the raw material solution collection passage is arranged in a top surface or an upper part wall surface of the reaction vessel. The silver salt solution may be collected from the reaction vessel by sucking the silver salt solution through the silver salt solution collection passage with a nozzle extending from a lower part of the reaction vessel, preferably a bottom surface of the reaction vessel. In the case where a silver salt solution collection passage and a raw material solution collection passage is provided with the reaction vessel, for the purpose of facilitate the collection of the silver salt solution and the raw material solution from the reaction vessel, it is preferred that the silver salt solution collection passage is connected to a part located below the raw material solution inlet port and the raw material solution collection passage is connected to a part located above the silver salt solution inlet port.

Preferred examples of the embodiment of the reaction vessel to be used in the present invention include a static fluid mixer (for example, a static mixer or an in-line mixer, which has a blade or a fin provided therein for mixing a fluid), a press-fit-type mixer (for example, an in-line mixer equipped with a venturi orifice), an element-laminated mixer (for example, an in-line mixer having a laminate with many through-holes for fluid mixing purposes), and a liquid-liquid extraction device equipped with a reaction column having a porous dispersion board or a stirrer. Specific examples of the static fluid mixer include a static mixer (T-3, -4 model, N10 model, N60 model; Noritake Co., Ltd.), an in-line mixer (TD model; HOKUTO MFG. CO., LTD.), and an OHR mixer (MX10 model; OHR Laboratory Corporation). A specific example of the press-fit-type mixer is a VR line mixer (VRX10, VRX20, etc.; Nagoya Oshima Machinery Co., Ltd.). A specific example of the element-laminated mixer is a MSE static mixer (ISEL CO., LTD.). A specific example of the liquid-liquid extract ion device is a liquid-liquid extract ion device disclosed in JP 2004-243203 A or JP 5-200260 A. However, examples of the reaction vessel to be used in the present invention are not limited to these devices.

The reaction vessel to be used in the method according to the present invention may be a single vessel, or may be a combination of two or more vessels which are in fluid-communication with each other. For example, it is possible to use a static fluid mixer, a press-fit-type mixer, an element-laminated mixer, and a liquid-liquid extraction device singly, or two or more of these devices in combination. In the case where two or more vessels are used in combination, the complex-containing silver salt solution collected from a first vessel is supplied into another vessel, and contacted with the raw material solution to form a complex, and the complex is accumulated. Subsequently, the silver salt solution is transferred to another vessel and is brought into contact with the raw material solution in the vessel, or is transferred to a distribution vessel or an extraction vessel as mentioned below.

In the organic phase (raw material solution) collected from the reaction vessel, a PUFA that has not been formed into a complex may be still contained. In this case, it is possible to supply the collected organic phase into the first reaction vessel or another reaction vessel, or additionally a further reaction vessel to contact the organic phase with the silver salt solution again, whereby the PUFA that has not been formed into a complex can be converted to a PUFA-silver complex and the PUFA-silver complex can be collected together with the silver salt solution. The silver salt solution thus obtained can be collected by partitioning the silver salt solution from the organic phase in the same manner as mentioned above. The collected silver salt solution may be combined with a silver salt solution that is obtained by the same procedure as that mentioned above and contains a PUFA-silver complex and the combined solution may be subjected to a PUFA alkyl ester extraction step as mentioned below, or the uncombined collected silver salt solution alone may be subjected to the extraction step.

It is preferred that the procedure of the method according to the present invention mentioned above is carried out under a low oxygen condition. The low oxygen condition can be achieved, for example, by blocking a system for the method according to the present invention (e.g., the reaction vessel, the supply passage, the collection passage, a distribution vessel) for the method of the present invention from the external air to produce a closed system, by placing the inside of, for example, the reaction vessel, the supply passage, the collection passage or the distribution vessel under a nitrogen atmosphere, or by filling, for example, the reaction vessel, the supply passage, the collection passage, or the distribution vessel with a liquid (the raw material solution or the silver salt solution). It is preferred that the reaction vessel, the supply passage, the collection passage or the distribution vessel is blocked from the external air to produce a closed system and the closed system is filled with the raw material solution or the silver salt solution. In the case where both of the supply and collection of the silver salt solution and the raw material solution in the reaction vessel are carried out in a continuous mode, the low oxygen state can be maintained once the system is filled with a liquid. The term "low oxygen condition" as used herein preferably refers to a condition where the oxygen concentration is less than 0.4%, more preferably a condition where the oxygen concentration is 0.1% or less. The method according to the present invention is preferably carried out under a light-shielded condition. When the method according to the present invention is carried out under a low oxygen condition and/or a light-shielded condition, a decrease in a pH value of the silver salt solution and oxidation of an oil or fat in the raw material solution or the silver salt solution can be prevented and deterioration of the silver salt solution or deterioration of a purified PUFA-containing composition can also be prevented.

(1-2. Extraction of PUFA Alkyl Ester)

A PUFA alkyl ester can be extracted from the silver salt solution which contains a complex of the PUFA and silver, and is collected in the above-mentioned manner using an organic solvent. Therefore, the method for producing the PUFA-containing composition according to the present invention may further include a step of extracting the PUFA alkyl ester from the silver salt solution collected from the reaction vessel using an organic solvent.

The procedure for extracting the PUFA alkyl ester can be carried out by, for example, the conventional process such as the methods disclosed in Patent Literatures 1 to 4. More specifically, the silver salt solution containing the PUFA-silver complex and being collected from the reaction vessel is contacted with an organic solvent. The PUFA alkyl ester in the silver salt solution can be extracted into the organic solvent through this contact. The organic solvent that has been contacted with the silver salt solution is collected to obtain the PUFA alkyl ester.

Examples of the organic solvent to be used for the extraction include solvents which have a high solubility of an alkyl ester (e.g., EPA, DHA and DPA) and can be separated from water, such as hexane, ether, ethyl acetate, butyl acetate, chloroform, cyclohexane, benzene, toluene and xylene. Among these solvents, hexane or cyclohexane is preferred.

It is preferred that the silver salt solution collected from the reaction vessel is transferred to a second reaction vessel (hereinafter also referred to as an "extraction vessel") for the purpose of contacting the silver salt solution with the organic solvent, and the silver salt solution is contacted with the organic solvent in the extraction vessel. The supply and collection of the silver salt solution or the organic solvent in the extraction vessel may be carried out in a batch mode, but is preferably carried out in a continuous mode. In the method according to the present invention, it is preferred that the supply of the organic solvent into the extraction vessel, the supply of the silver salt solution collected from the reaction vessel into the extraction vessel, the contact of the silver salt solution with the organic solvent and the collection of the contacted organic solvent and silver salt solution from the extraction vessel are carried out concurrently with one another.

The supply of the silver salt solution into the extraction vessel is carried out through a flow path through which the above-mentioned reaction vessel or distribution vessel is in fluid-communication with the extraction vessel (the flow path is hereinafter also referred to as a "communication passage"). The supply of the organic solvent into the extraction vessel is preferably carried out through a flow path through which a supply source of the organic solvent is in fluid-communication with the extraction vessel (the flow path is hereinafter also referred to as an "organic solvent supply passage"). Each of the communication passage and the organic solvent supply passage may be provided with, for example, a valve, a pump, and a valve. Each of the communication passage and the organic solvent supply passage may be connected to the extraction vessel directly. Alternatively, the communication passage and the organic solvent supply passage may be connected to each other collectively and then connected to the extraction vessel.

The silver salt solution and the organic solvent supplied to the extraction vessel may form a continuous phase or a dispersed phase, respectively, in the extraction vessel. In one embodiment, the organic solvent exists in a form of a continuous phase and the silver salt solution exists in a form of a dispersed phase in the extraction vessel. In this case, the dispersed phase of the silver salt solution may be preferably in a form of liquid droplets dispersed in the continuous phase of the organic solvent. In another embodiment, the organic solvent exists in a form of a dispersed phase and the silver salt solution exists in a form of a continuous phase in the extraction vessel. In this case, the dispersed phase of the organic solvent may be preferably in a form of liquid droplets dispersed in the continuous phase of the silver salt solution. For formation of the dispersed phase of the silver salt solution or the organic solvent, any method capable of dispersing a liquid as mentioned in (1-1) can be employed. Alternatively, each of the silver salt solution and the organic solvent exits in a form of a continuous phase. In one embodiment, the silver salt solution in the extraction vessel flows through the continuous phase of the organic solvent. In another embodiment, each liquid flow of the silver salt solution and the organic solvent exists in the extraction vessel and the liquid flows may be countercurrent or parallel and may be in contact with each other.

Preferred examples of the extraction vessel include a static fluid mixer, a press-fit-type mixer, an element-laminated mixer and a liquid-liquid extraction device which are mentioned in (1-1). The extraction vessel may be composed of a single vessel, or may be composed of a combination of two or more vessels which are in fluid-communication with each other. For example, a static fluid mixer, a press-fit-type mixer, an element-laminated mixer, and a liquid-liquid extraction device as mentioned above may be used singly, or a combination of two or more of them may be used. In the case where two or more vessels are used in combination, the silver salt solution collected from a first vessel is supplied into another vessel, and contacted with an organic solvent in the vessel to extract a remaining PUFA. Subsequently, the silver salt solution may be transferred to an additional extraction vessel or a distribution vessel and collected, if necessary.

The temperature of the silver salt solution upon contact with an organic solvent is preferably from 30 to 80° C., more preferably from 50 to 70° C. Examples of a method for keeping the temperature of the silver salt solution within the above-mentioned range upon contact with an organic solvent include a method in which the silver salt solution and/or the organic solvent is warmed to a temperature falling within the above-mentioned range and then these solutions are contacted with each other, and a method in which the temperature of the extraction vessel is kept within the above-mentioned range, and a combination of these methods.

The extraction of the PUFA alkyl ester can be accelerated by increasing the contact frequency of the silver salt solution with the organic solvent in the extraction vessel. In a preferred embodiment, the size of the extraction vessel is as follows: the volume is about from 1 cm$^3$ to 10 m$^3$ and the distance between an inlet port and a collection port for the silver salt solution or the organic solvent in the extraction vessel is about from 15 to 400 cm. It is preferred that the flow amount of the silver salt solution to be supplied to and to be collected from the extraction vessel is preferably about from 100 to 5000 g/sec. It is preferred that the volume ratio between the silver salt solution and the organic solvent which flow in the extraction vessel is adjusted to about 1:1 to 3. It is preferred that either of the silver salt solution and the organic solvent in the extraction vessel forms a dispersed phase and the other forms a continuous phase. Regardless of which forms a dispersed phase, the dispersed phase in the extraction vessel is prepared in a form of liquid droplets preferably each having a particle diameter of about 0.05 to 5 mm. The retention time of the silver salt solution and the organic solvent in the extraction vessel is preferably about from 1 to 300 seconds, regardless of the form, a dispersed phase or a continuous phase.

A PUFA alkyl ester in the silver salt solution can be extracted into an organic solvent by the contact of the silver salt solution with the organic solvent. The contacted silver salt solution and the organic solvent may be collected from the extraction vessel together or may be collected separately. The collection of the silver salt solution and the organic solvent from the extraction vessel preferably can be carried out in the same manner as that employed for the collection of a liquid from the reaction vessel as mentioned in (1-1) above.

For example, in the case where the silver salt solution and the organic solvent are collected together, the organic solvent containing the PUFA alkyl ester is fractionated from the collected liquid. It is preferred that the liquid collected from the extraction vessel is transferred to a second distribution vessel and is then distributed into a phase of the organic solvent (an organic phase) and a phase of the silver salt solution (an aqueous phase). The organic solvent containing a PUFA alkyl ester can be collected by fractionating the distributed organic phase. Furthermore, the used silver salt solution can be collected by fractionating the distributed aqueous phase. The collection of the silver salt solution or the organic solvent from the second distribution vessel can be achieved through each of the collection passage connected to the distribution vessel. For facilitating the collection of the distributed organic phase and aqueous phase, it is preferred that an outlet port for the silver salt solution from the second distribution vessel is arranged on a bottom surface or a lower wall surface of the distribution vessel, and an outlet port for the organic solvent is arranged on a top surface or an upper wall surface of the distribution vessel. It is also preferred that the silver salt solution may be sucked through a nozzle arranged at a lower part, preferably on a bottom surface, of the second distribution vessel and may be collected from the distribution vessel and the organic solvent may be sucked through a nozzle arranged at an upper part of the second distribution vessel and may be collected from the distribution vessel.

For example, in the case where the silver salt solution and the organic solvent are collected from the extraction vessel separately, it is preferred that a silver salt solution collection passage is arranged on the bottom surface or a lower wall surface of the extraction vessel, while an organic solvent collection passage is arranged on a top surface or an upper wall surface of the extraction vessel. For facilitating the collection of the silver salt solution and the organic solvent after the reaction, it is preferred that the silver salt solution collection passage is connected to a part located below the organic solvent inlet port, and the organic solvent collection passage is connected to a part above the silver salt solution inlet port.

In order to prevent the oxidation of the extracted PUFA alkyl ester or the silver salt solution, it is preferred that the above-mentioned PUFA alkyl ester extraction procedures are also carried out under a low oxygen condition and/or a light-shielded condition. It is preferred that the system for the procedures (e.g., an extraction vessel, a communication passage, an organic solvent supply passage, a collect ion passage, a second distribution vessel) is placed under a low oxygen condition and/or a light-shielded condition. The low oxygen condition can be achieved in the same manner as those mentioned in (1-1).

(1-3. Prevention of Deterioration of Silver Salt Solution and Re-use Thereof)

In the method for producing the PUFA-containing composition according to the present invention, a decrease in a pH value of the silver salt solution, oxidation of an oil or fat in the raw material solution and the silver salt solution, deterioration of the silver salt solution thereby, and deterioration of a purified PUFA-containing composition can be greatly prevented by carrying out a process for the supply and collection of the silver salt solution in the reaction vessel and optionally processes for the supply and collection of the silver salt solution in the extraction vessel concurrently with each other (that is, in a continuous mode), preferably by carrying out processes starting from the supply of the silver salt solution to the reaction vessel until the collection of the silver salt solution from the extraction vessel in a continuous mode. For example, in the conventional batch mode, it is believed that the silver salt solution tends to be oxidized during stirring-mixing of the raw material solution with the silver salt solution in the reaction vessel and during batch collection of the silver salt solution after the reaction, and this oxidation may deteriorate the silver salt solution. On the other hand, in a continuous mode as in the case of the present invention, it becomes possible to extremely reduce the chance of the contact between the silver salt solution with external air in the reaction vessel or during the collection of the silver salt solution after the reaction, and therefore deterioration of the silver salt solution due to oxidation can be prevented.

Therefore, in the method according to the present invention, the silver salt solution collected from the extraction vessel can be re-used. More specifically, in the method according to the present invention, the silver salt solution collected from the extraction vessel can be supplied to the reaction vessel again directly or after being adjusted for the concentration of silver salt properly, thereby being contacted with the raw material solution. In a preferred embodiment of the method of the present invention, the silver salt solution to be supplied to the reaction vessel contains a silver salt solution that has been collected from the extraction vessel after the contact with the organic solvent.

Therefore, in a preferred embodiment, the method for producing the PUFA-containing composition according to the present invention can be a method in which the contact of the silver salt solution with the raw material solution and the contact of a silver salt solution containing a complex thus produced with the organic solvent are carried out continuously while circulating the silver salt solution between the reaction vessel and the extraction vessel. In this method, the silver salt solution collected from the reaction vessel is contacted with the organic solvent, a PUFA alkyl ester is extracted from the silver salt solution, and then the silver salt solution that had been contacted with the organic solvent is collected from the extraction vessel and is supplied again to the reaction vessel. The silver salt solution that has been supplied to the reaction vessel again is contacted with the raw material solution to form a PUFA-silver complex. In the method according to the present invention, the silver salt solution can be used repeatedly preferably 10 times or more, more preferably 30 times or more, still more preferably 70 times or more, still more preferably 100 times or more, still more preferably 300 times or more. In this regard, the term "use" as used herein in association with the repeated use of the silver salt solution refers to a series of processes starting from the supply of the silver salt solution into the reaction vessel and until the collection thereof from the extraction vessel, and the phrase "the series of processes is carried out one round" corresponds to that the silver salt solution is used "once". In one round of the processes, the time during which the silver salt solution is in contact with the PUFA (a PUFA contact time as mentioned in the Examples described below, that is, the time between a time point at which the silver salt solution is supplied to the raw material solution and a time point at which a PUFA ethyl ester-containing composition is extracted from the silver salt solution using an organic solvent) is preferably 10 minutes or shorter, more preferably 5 minutes or shorter, on average.

The degree of deterioration of the silver salt solution can be measured by employing, as an index, a pH value or a color of the silver salt solution, an amount of a free fatty acid contained in the silver salt solution, or a pH value or a Gardner color scale of the solution, or the like. For example, an unused silver salt solution generally has a pH value of around 7, is colorless and transparent, and contains no free fatty acid. However, when the silver salt solution is deteriorated with an increased use, it is reduced in the pH value thereof, is discolored into a yellowish or brownish color, and is increased in the amount of free fatty acids. The amount of free fatty acids in a solution can be measured by the method mentioned in Reference Example 2 below. According to the method of the present invention, the amount of free fatty acids in the silver salt solution that has been used repeatedly in 10 rounds of the series of process for forming a complex and extracting a PUFA alkyl ester can be reduced to preferably 5 mEq/L or less, more preferably 3 mEq/L or less. Still more preferably, the amount of free fatty acids in the silver salt solution that is used repeatedly 100 rounds of the series of processes can be reduced to preferably 50 mEq/L or less, more preferably 20 mEq/L or less.

The Gardner color scale of the silver salt solution can be measured in accordance with Japanese Industrial Standards, JIS K0071 "Testing Method for Color of Chemical Products". A higher Gardner color scale of a solution means that the silver salt solution is further deteriorated. The Gardner color scale of the silver salt solution used in the method of the present invention is about 5 even after used repeatedly about 30 times or more, and is never 9 or more even after used further repeatedly. In contrast, the Gardner color scale of the silver salt solution that is used in the conventional batch method is increased to 11 or more when used repeatedly about 15 times. These results mean that the silver salt solution is hardly deteriorated in the method of the present invention, as compared with a batch method.

In the method for producing the PUFA-containing composition according to the present invention, a continuous mode is employed and the silver salt solution is re-used, and therefore it becomes possible to reduce the amount of the silver salt solution required for extraction of a PUFA, as compared with the conventional method (a batch-mode). In a preferred embodiment, in the method according to the present invention, the amount of the silver salt solution which is required for the extraction of a PUFA can be reduced to about ½ to ¹⁄₂₀, preferably about ⅕ to ¹⁄₁₀, as compared with the conventional method.

(1-4. Separation of PUFA-containing Composition)

In the present invention, the organic solvent containing a PUFA alkyl ester that has been collected by the above-mentioned procedure can be obtained as a PUFA-containing composition. The PUFA-containing composition contains an alkyl ester of a PUFA, preferably EPA, AA, ETA, DHA or DPA, separated from the raw material solution. If necessary, the collected organic solvent may be further purified by, for example, concentration, chromatography, or distillation. The PUFA-containing composition obtained by the method according to the present invention preferably contains an alkyl ester of at least one PUFA selected from the group consisting of EPA, DHA and DPA, more preferably an alkyl ester of EPA and/or DHA, in an amount of 70% by mass or more, more preferably 80% by mass or more, and still more preferably contains an alkyl ester of EPA in an amount of 50% by mass or more, more preferably 70% by mass or more, in the total fatty acids contained.

In the method according to the present invention, the collected organic solvent from which a PUFA alkyl ester is separated by, for example, concentration, chromatography, distillation can be re-used for extraction of a PUFA alkyl ester. More specifically, the organic solvent from which a PUFA alkyl ester is separated can be supplied into the extraction vessel again directly or after being mixed with a fresh organic solvent, thereby being in contact with the silver salt solution.

In the method for producing the PUFA-containing composition by a continuous mode according to the present invention, it is not needed to carry out an operation for collecting a complex-containing silver salt solution or a PUFA-containing organic solvent unlike the conventional method (a batch-mode), and it is not needed to halt a complex production reaction or a PUFA extraction operation for the collection, either. Furthermore, in the method according to the present invention, the deterioration of the silver salt solution can be inhibited, and the amount of the silver salt solution to be used can be reduced. Therefore, the present invention can provide a high-efficient and low-cost PUFA production method.

(2. Apparatus for Producing PUFA-containing Composition)

As preferred embodiments of the present invention, schematic diagrams of the procedure for producing a PUFA-containing composition using parallel-flow-mode and counter-flow-mode apparatus for producing PUFA-containing composition are disclosed in FIGS. 1 to 3.

FIG. 1A shows a schematic diagram of a parallel-flow-mode apparatus for producing PUFA-containing composition. In FIG. 1A, a reaction vessel and an extraction vessel is a static fluid mixer, and includes a blade therein for fluid mixing purposes. The reaction vessel is in fluid-communication with a raw material solution supply source and a silver salt solution supply source. A raw material solution and a silver salt solution supplied into the reaction vessel are mixed by a stirring action of the blade so as to contact with each other. Liquid droplets of the raw material solution or the silver salt solution can be produced by adjusting the amounts of the raw material solution and the silver salt solution to be stirred. In one embodiment, the raw material solution forms a continuous phase and the silver salt solution is in a form of liquid droplets in the reaction vessel. In another embodiment, the raw material solution is in a form of liquid droplets and the silver salt solution forms a continuous phase in the reaction vessel. In another embodiment, both of the raw material solution and the silver salt solution form a continuous phase in the reaction vessel. The reaction vessel is connected to a distribution vessel (1) on the opposite side of a liquid inlet port, and therefore a liquid supplied into the reaction vessel can be delivered to the distribution vessel (1) little by little. In the distribution vessel (1), the raw material solution (organic phase) is separated as an upper layer and the complex-containing silver salt solution (aqueous phase) is separated as a lower layer. The raw material solution in the upper layer is collected, and the silver salt solution in the lower layer is transferred into the extraction vessel.

In FIG. 1A, the extraction vessel is in fluid-communication with the lower layer in the distribution vessel (1) and the organic solvent supply source. A raw material solution and a silver salt solution supplied into the extraction vessel are mixed by a stirring action of the blade so as to contact with each other. In one embodiment, the organic solvent forms a continuous phase and the silver salt solution is in a form of liquid droplets in the extraction vessel. In another embodiment, the organic solvent is in a form of liquid droplets and the silver salt solution forms a continuous phase in the extraction vessel. In another embodiment, both of the organic solvent and the silver salt solution form a continuous phase in the extraction vessel. The extraction vessel is connected to a distribution vessel (2) on the opposite side of a liquid inlet port, and therefore a liquid supplied into the extraction vessel can be delivered to the distribution vessel (2) little by little. In the distribution vessel (2), the organic solvent containing a PUFA (organic phase) is separated as an upper layer and the silver salt solution (aqueous phase) is separated as a lower layer. The organic solvent in the upper layer is collected, and the PUFA-containing composition is purified or concentrated. The silver salt solution in the lower layer is returned to the silver salt solution supply source, and is then supplied into the reaction vessel again.

FIG. 1B is a schematic diagram illustrating only a part, a reaction vessel and a distribution vessel (1), of the apparatus for producing a PUFA-containing composition production which has the same structure as that shown in FIG. 1A. In the apparatus shown in FIG. 1B, a pathway through which the raw material solution (organic phase) collected from the distribution vessel (1) is returned to the reaction vessel is provided.

FIG. 2 shows a schematic diagram of a counter-flow-mode apparatus for producing a PUFA-containing composition. In FIG. 2, a reaction vessel and an extraction vessel is a reaction column. The react ion vessel is in fluid-communication with a raw material solution supply source and a silver salt solution supply source. The silver salt solution is supplied from an upper part of the reaction vessel and then moves downward therein, and the raw material solution is supplied from a lower part of the reaction vessel and moves upward therein. As a result, a countercurrent flow occurs to contact the raw material solution and the silver salt solution. The silver salt solution is in a form of liquid droplets (dispersed phase) during the transfer, and is accumulated in a lower layer of the reaction vessel to form a continuous aqueous phase. The continuous aqueous phase is delivered into the extraction vessel. The raw material solution is collected from an upper part of the reaction vessel.

In FIG. 2, the extraction vessel is in fluid-communication with the lower layer of the react ion vessel and the organic solvent supply source. The silver salt solution collected from the reaction vessel is supplied from an upper part of the extraction vessel and moves downward therein, and the organic solvent is supplied from a lower part of the extraction vessel and moves upward therein. As a result, a countercurrent flow occurs to contact the organic solvent and the silver salt solution. The silver salt solution is in a form of liquid droplets (dispersed phase) during the transfer, and is accumulated in a lower layer of the reaction vessel to form a continuous aqueous phase. The organic solvent in the upper layer is collected, and the PUFA-containing composition is purified or concentrated. The silver salt solution in the lower layer is returned to the silver salt solution supply source, and is then supplied into the reaction vessel again.

FIG. 3 shows a schematic diagram of another counter-flow-mode apparatus for producing a PUFA-containing composition. The basic constitution of the apparatus shown in FIG. 3 is substantially the same as that of the apparatus shown in FIG. 2, except that a silver salt solution in a reaction vessel and an extraction vessel forms a continuous phase and a raw material solution and an organic solvent is in a form of liquid droplets (dispersed phase) in FIG. 3.

In FIGS. 1 to 3, the reaction vessel, the extraction vessel, the distribution vessel and flow paths connecting these vessels are a closed system and are filled with a liquid. As shown in FIG. 1, the internal temperature of the reaction vessel and the extraction vessel can be controlled by means of a cooling medium or a heating medium provided therein. Furthermore, as shown in FIG. 1, the speed and amount of a liquid to be supplied into and collected from the reaction vessel and the extraction vessel can be controlled by means of a pump. The silver salt solution shown in FIGS. 2 to 3 can fall freely under gravity, but the contact frequency between the raw material solution and the silver salt solution can be controlled by adjusting the size of the liquid droplets or the amount to be discharged. In the apparatuses shown in FIGS. 1 to 3, the flow amount of the silver salt solution to be supplied into and collected from the reaction vessel and the extraction vessel is preferably about from 100 to 5000 g/sec. In the case where the silver salt solution forms a dispersed phase in the reaction vessel and the extraction vessel, it is preferred to modify the silver salt solution to be in a form of liquid droplets each having a particle diameter of about 0.05 to 5 mm.

In a preferred embodiment, the size of the reaction vessel and the extraction vessel in each of the apparatuses shown in FIGS. 1 to 3 is as follows: the volume is about 1 $cm^3$ to 10 $m^3$, and the distance between an inlet port and a collection port for the silver salt solution in each of the reaction vessel and the extraction vessel is about from 15 to 400 cm. The PUFA contact time of the silver salt solution in the apparatuses shown in FIGS. 1 to 3 is preferably 10 minutes or shorter, more preferably 5 minutes or shorter, per use once on average. As shown in FIGS. 1 to 3, in the method for producing the PUFA-containing composition employed in the present invention, the supply and the collection of the silver salt solution in the reaction vessel and the extraction vessel are carried out in parallel and continuously so that the continuous extraction of a PUFA-containing composition can be achieved. Therefore, use of a large-scale reaction vessel that has been used in the conventional batch-mode is unnecessary. According to the present invention, it becomes possible to reduce the size of a facility needed for the production of a PUFA.

(3. Exemplary Embodiment of Method for Producing PUFA-containing Composition in Counter-flow-mode)

(3-1. Production Method)

In this section, an exemplary embodiment of the method for producing a PUFA-containing composition in counter-flow-mode according to the present invention is disclosed. The method according to the present invention according to this embodiment include:

supplying a aqueous solution containing a silver salt to a raw material solution containing an alkyl ester of the PUFA to fall the aqueous solution containing a silver salt downward in the raw material solution, thereby contacting the aqueous solution containing a silver salt with the raw material solution; and collecting the aqueous solution that has been contacted with the raw material solution.

According to the method of this embodiment, purification of the polyunsaturated fatty acid using a silver salt can be carried out continuously. In this method, the amount of the silver-salt-containing aqueous solution to be used can be reduced, and an operation for collecting the silver-salt-containing aqueous solution batch at every collection of polyunsaturated fatty acid can be eliminated. This method can improve the efficiency and cost required for producing a polyunsaturated fatty acid.

In the method according to this embodiment, the temperature of the silver salt solution upon contact with a raw material solution containing an alkyl ester of the PUFA is preferably from 5 to 30° C., more preferably from 15 to 30° C. Examples of a method for keeping the temperature of the silver salt solution within the above-mentioned range upon contact with the raw material solution include a method in which the raw material solution and/or the silver salt solution is warmed or cooled to a temperature falling within the above-mentioned range and then these solution are contacted with each other, a method in which the temperature of the reaction vessel for contact of the raw material solution and the silver salt solution is kept within the above-mentioned range, and a combination of these methods.

It is preferred that the raw material solution containing an alkyl ester of the PUFA forms a continuous phase having a specific height in the reaction vessel. The silver salt solution may be a continuous phase that runs through the continuous phase of the raw material solution, and is preferably a dispersed phase. The dispersed phase may be in a form of liquid droplets or mists. For formation of the dispersed phase of the silver salt solution, any method capable of dispersing an aqueous solution can be employed. For example, a method of spraying a solution through a nozzle of the like, a method of applying vibrations to an inlet pathway for the silver slat solution using a vibrator to make the silver salt solution more fine, and a method of using a liquid distributor or a porous dispersion board to make the silver salt solution more fine can be employed. The silver salt solution can be supplied to the continuous phase of the raw material solution, a top surface thereof, or a part located above the continuous phase, and is preferably supplied to an upper part in the continuous phase of the raw material solution.

In the method of this embodiment, when the silver salt solution is supplied to the raw material solution in the reaction vessel, the silver salt solution is contacted with the raw material solution while falling downward in the raw material solution due to the difference in specific gravity. This contact leads to formation of a PUFA-silver complex.

When the contact time of the silver salt solution with the raw material solution (retention time in the raw material solution) is longer, formation of a complex of a PUFA and a silver salt can be promoted. The contact time can be varied by altering, for example, the height of the continuous phase of the raw material solution, the flow rate of the silver salt solution, or the size of the dispersed phase of the silver salt solution (for example, the particle diameters of the liquid droplets). For example, the raw material solution is prepared into a continuous phase having a height of 30 cm or more, preferably a height of 50 to 300 cm, and the silver salt solution is prepared into liquid droplets each having a particle diameter of about 0.01 to 0.2 cm. For example, when a nozzle is used for forming the dispersed phase, the silver salt solution is added dropwise to the raw material solution at a flow amount of 0.1 to 50 g/min per nozzle when a nozzle. The flow amount can be increased by placing nozzles at multiple sites. The height of the continuous phase of the raw material solution refers to the maximum distance at which the raw material solution is in contact with the silver salt solution, for example, a distance from the position of a silver salt solution inlet port located at an upper part of the reaction vessel to an interface between the aqueous phase of the silver salt solution formed at a lower part of the reaction vessel and the raw material solution.

The PUFA-silver complex thus formed moves downward together with the silver salt solution to be dissolved in the silver salt solution. Finally, the complex-containing silver salt solution forms an aqueous phase that is heavier than the raw material solution. That is, in the method of this embodiment, the silver salt solution supplied into the reaction vessel extracts a complex of a PUFA and a silver salt while falling downward in the raw material solution, and then forms an aqueous phase containing the complex at the bottom of the reaction vessel. Therefore, in this method, the silver salt solution that has not been reacted with a PUFA yet and the silver salt solution that has been reacted there are separated into different phases, respectively without being mixed. This makes it possible to collecting the silver salt solution that has been contacted with the raw material solution, independently supplying the silver salt solution to the raw material solution.

Therefore, in the method of this embodiment, the supply of the silver salt solution into the raw material solution and the collection of the silver salt solution that has been contacted with the raw material solution can be carried out concurrently with each other. That is, in this method, it is not needed to replace the whole of the silver salt solution in the reaction vessel unlike the conventional method, and the collection of the contacted aqueous solution can be continued while continuing the supply to and the contact with the raw material solution, of the silver salt solution. In this method, the supply into and the correction from the raw material solution, of the silver salt solution, may be carried out continuously or intermittently. The timing of the supply and the collection may be made coincident with each other, or these timings may be set independently. It is preferred that, in this method, the supply and the correction from the raw material solution, of the silver salt solution, are carried out continuously.

The collection of the silver salt solution that has been contacted with the raw material solution can be carried out by, for example, sucking the solution through a sucking tube, by flowing out the aqueous phase through an outlet port provided at a lower part of the reaction vessel.

In one aspect of the method of this embodiment, the raw material solution containing an alkyl ester of the PUFA can also be supplied into the reaction vessel continuously or intermittently. It is preferred that the raw material solution is supplied from a lower part of the reaction vessel to be contacted with the silver salt solution and is then discharged from an upper part of the reaction vessel. It is preferred that the raw material solution is discharged from the reaction vessel through a discharge port provided at an upper part of the reaction vessel. The supply of and correction of the raw material solution may be carried out continuously or intermittently, and the timings of the supply and collection may be made coincident with the timings of those of the silver salt solution or may be set independently from these timings.

In the method according to this embodiment, subsequently a PUFA alkyl ester is extracted using an organic solvent from the PUFA-silver complex-containing silver salt solution, which is prepared in the above-mentioned procedure. The procedure for the extraction can be carried out in accordance with the method disclosed in Patent Literatures 1 to 4. Examples of the organic solvent to be used in this procedure include solvents which have a high solubility of an alkyl ester including, for example, EPA, DHA, or DPA and can be separated from water, such as hexane, ether, ethyl acetate, butyl acetate, chloroform, cyclohexane, benzene, toluene and xylene. Among these solvents, hexane or cyclohexane is preferred.

In the method according to this embodiment, it is preferred that the PUFA-silver complex-containing silver salt solution that has been contacted with the raw material solution is then delivered into a second reaction vessel (that is, an extraction vessel) and is supplied to the organic solvent in the second reaction vessel. The supplied silver salt solution falls downward in the organic solvent due to the difference in specific gravity to be in contact with the organic solvent. This contact leads to extraction of a PUFA alkyl ester in the silver salt solution into the organic solvent.

The temperature of the silver salt solution upon contact with the organic solvent is preferably 30 to 80° C., more preferably 50 to 70° C. Examples of a method for keeping the temperature of the silver salt solution within the above-mentioned range upon the contact with the organic solvent include a method in which the temperature of the silver salt solution and/or the organic solvent is warmed to a temperature falling within the above-mentioned range and then they are contacted with each other, a method in which the temperature of the reaction vessel for the contact of the silver salt solution with the organic solvent is kept within the above-mentioned range, and a combination of these methods.

It is preferred that the organic solvent forms a continuous phase having a specific height in the second reaction vessel. The silver salt solution to be contacted with the organic solvent may be a continuous phase that penetrates through the continuous phase composed of the organic solvent, and preferably forms a dispersed phase. The dispersed phase may have the form of liquid droplets or mists, and can be formed by any method for dispersing the silver salt solution. The silver salt solution can be supplied to the continuous phase of the organic solvent, a top surface of the continuous phase, or a part located above the upper surface of the continuous phase, and is preferably supplied to an upper part in the continuous phase of the organic solvent.

When the contact time of the silver salt solution with the organic solvent (retention time in the organic solvent) is longer, extraction of a PUFA alkyl ester into the organic solvent can be promoted. The contact time can be varied by altering, for example, the height of the continuous phase of the organic solvent, or the size of the dispersed phase of the silver salt solution (for example, the particle diameters of the liquid droplets). For example, the organic solvent is prepared into a continuous phase having a height of 30 cm or more, preferably a height of 50 to 300 cm, and the silver salt solution is prepared into liquid droplets each having a particle diameter of about 0.01 to 0.2 cm. For example, when a nozzle is used for forming the dispersed phase, the silver salt solution is added dropwise to the organic solvent at a flow amount of 0.1 to 50 g/min per nozzle. The height of the continuous phase of the organic solvent refers to the maximum distance at which the organic solvent is in contact with the silver salt solution, e.g., a distance from the position of a silver salt solution inlet port located at an upper part of the reaction vessel to an interface between the aqueous phase of the silver salt solution formed at a lower part of the reaction vessel and the organic phase.

The organic solvent containing a PUFA alkyl ester can be obtained by collecting the organic solvent that has been contacted with the silver salt solution. It is preferred to collect an upper layer in the organic solvent in the second reaction vessel. It is preferred that the organic solvent is supplied from a lower part of the second reaction vessel to be contacted with the silver salt solution and is then collected from an upper part of the reaction vessel. The collection of the organic solvent can be carried out by sucking an upper layer of the organic solvent through for example, a sucking tube, or by flowing out the organic solvent through an outlet port provided at an upper part of the second reaction vessel.

The collected organic solvent is obtained as a PUFA-containing composition. The composition contains an alkyl ester of a PUFA, preferably EPA, AA, ETA, DHA or DPA, separated from the raw material solution. If necessary, the collected organic solvent may be further purified by, for example, distillation. The PUFA-containing composition obtained by the method according to this embodiment preferably contains an alkyl ester of at least one PUFA selected from the group consisting of EPA, DHA and DPA, more preferably an alkyl ester of EPA and/or DHA, in an amount of 70% by mass or more, more preferably 80% by mass or more, and still more preferably contains an alkyl ester of EPA in an amount of 50% by mass or more, more preferably 70% by mass or more, in the total fatty acids contained.

The silver salt solution that has been contacted with the organic solvent in the second reaction vessel forms an aqueous phase at the bottom of the organic solvent, and therefore can be discharged easily from the reaction vessel. It is preferred that the raw material solution is discharged from the reaction vessel through a discharge port provided at a lower part of the second reaction vessel. On the other hand, the organic solvent is collected from the second reaction vessel while a fresh one of the organic solvent is supplied. It is preferred that the fresh one is supplied from a lower part of the second reaction vessel.

It is preferred that the supply and collection of the silver salt solution and the organic solvent in the second reaction vessel are carried out continuously or intermittently, the timing of the supply and the correction may be made coincident with each other, or these timings may be set independently from each other. More preferably, the supply and the collection are carried out continuously.

In the method according to this embodiment, the supply of the silver salt solution to the organic solvent and the collection of the organic solvent are carried out concurrently with each other. That is, in this method, it is possible to continue the collection of the contacted organic solvent or aqueous solution while continuing the supply of the organic solvent to the silver salt solution and the contact of them. It is preferred that all of the supply and collection of the silver salt solution and the organic solvent are carried out concurrently with each other.

In a more preferred aspect of the method according to this embodiment, in the step of contacting the raw material solution with an aqueous solution containing a silver salt, the aqueous solution is supplied from an upper part of the first reaction vessel and the raw material solution containing the alkyl ester of the PUFA is supplied from a lower part of the first reaction vessel. The aqueous solution and the raw material solution thus supplied move downward and upward, respectively, due to the difference in specific gravities thereof. As a result, the aqueous solution and the raw material solution flow concurrently to each other in the reaction vessel to be contacted with each other. It is preferred that the raw material solution forms a continuous phase, while the aqueous solution flows downward through the continuous phase of the raw material solution. The aqueous solution may be a continuous phase, but is preferably a dispersed phase. The aqueous solution that passes through the phase of the raw material solution forms an aqueous phase containing a complex of a PUFA and a silver salt below the phase of the raw material solution. Therefore, the aqueous phase can be collected from lower part below the raw material solution inlet port in the reaction vessel. It is preferred that an outlet port through which the aqueous phase is collected is provided at apart below the raw material solution inlet port in the reaction vessel, and the aqueous phase can be collected through the outlet port.

In a still more preferred aspect of the method according to this embodiment, in the step of contacting the organic solvent with the aqueous solution, the aqueous solution is supplied from an upper part of a second reaction vessel and the organic solvent is supplied from a lower part of the second reaction vessel. The aqueous solution and the organic solvent thus supplied move downward and upward, respectively, due to the difference in specific gravities thereof. As a result, the aqueous solution and the organic solvent flow concurrently in the reaction vessel to be contacted with each other. It is preferred that the organic solvent forms a continuous phase, while the aqueous solution flows downward through the continuous phase of the organic solvent. The aqueous solution may be a continuous phase, but is preferably a dispersed phase. The organic solvent can form an organic phase above the phase of the aqueous solution, while the aqueous solution forms an aqueous phase below the phase of the organic solvent. Therefore, the organic phase can be collected from a part above the aqueous solution inlet port in the second reaction vessel, while the aqueous phase can be collected from a part below the organic solvent inlet port in the reaction vessel. It is preferred that an outlet port through which the aqueous phase is collected is provided at a part below the organic solvent inlet port in the reaction vessel, to collect the aqueous phase through the outlet port, while an outlet port through which the organic phase is collected is provided at a part above the aqueous solution inlet port in the reaction vessel to collect the organic phase through the outlet port. The organic phase collected from the second reaction vessel is further purified as required, and is obtained as a PUFA-containing composition.

For example, in the method according to this embodiment, the silver salt solution that has been contacted with the organic solvent discharged from the second reaction vessel may be collected and then contacted with a fresh organic solvent in an additional reaction vessel in the same procedure as mentioned above. Furthermore, the step of contacting with a fresh organic solvent may be repeated at least two times or more.

It is preferred that the silver salt solution is subjected to a series of steps of contacting with the organic solvent, is then collected, and is re-used in the above-mentioned step of contacting with the raw material solution. The collected aqueous solution may be delivered to the first reaction vessel and is supplied to the raw material solution directly, or after being adjusted for the concentration of the silver salt properly to be re-used. Therefore, it is preferred that the silver salt solution to be supplied to the raw material solution in the first reaction vessel contains the aqueous solution collected from the second reaction vessel (or additional reaction vessel) after the contact with the organic solvent.

Therefore, the method for producing the PUFA-containing composition according to this embodiment may be a method in which the contact of the silver salt solution with the raw material solution and the contact of the silver salt solution containing a PUFA-silver complex produced thereby with the organic solvent are carried out continuously while circulating the silver salt solution between the first reaction vessel and a second reaction vessel (or additional reaction vessel).

It is preferred that the reaction vessel in which the raw material solution is contacted with the silver salt solution (a first reaction vessel) and the reaction vessel in which the organic solvent is contacted with the silver salt solution (a second and further reaction vessels) is a closed system. It is also preferred that these reaction vessels are light-shielded. Furthermore, these reaction vessels may be placed under a nitrogen atmosphere. When these reaction vessels are used, oxidation of a PUFA and a silver salt can be prevented.

(3-2. Production Apparatus)

An exemplary embodiment of the apparatus for producing a PUFA-containing composition based on the contact of the silver salt solution with the raw material solution and the contact of the silver salt solution with the organic solvent in a countercurrent mode as mentioned in (3-1) above will be disclosed.

In one embodiment, the apparatus for producing the PUFA-containing composition includes a first reaction vessel, wherein the first reaction vessel includes a raw material solution inlet port through which a raw material solution containing an alkyl ester of the polyunsaturated fatty acid is to be supplied into the reaction vessel, an aqueous solution inlet port through which an aqueous solution containing a silver salt is to be supplied into the reaction vessel, an aqueous solution collection port through which the aqueous solution that has been contacted with the raw material solution is to be collected, and a raw material solution collection port through which the raw material solution that has been contacted with the aqueous solution is to be collected, the raw material solution inlet port is arranged at the lower part of the first reaction vessel and above the aqueous solution collection port, and the aqueous solution inlet port is arranged at the upper part of the first reaction vessel, above the raw material solution inlet port and below the raw material solution collection port. In this apparatus, the aqueous solution which has been supplied through the aqueous solution inlet port flows downward in the first reaction vessel and the raw material solution which has been supplied through the raw material solution inlet port flows upward in the first reaction vessel. As a result, the aqueous solution and the raw material solution flowing countercurrently to each other in the first reaction vessel to contact with each other, and the contacted aqueous solution is collected outside the reaction vessel through the aqueous solution collection port.

In another embodiment, the apparatus for producing the PUFA-containing composition further includes a second reaction vessel, the second reaction vessel includes an organic solvent inlet port through which an organic solvent is to be supplied into the reaction vessel, an aqueous solution inlet port through which an aqueous solution collected through the aqueous solution collection port is to be supplied into the reaction vessel, an aqueous solution collection port through which the aqueous solution that has been contacted with the organic solvent is to be collected, and an organic solvent collection port through which the organic solvent that has been contacted with the aqueous solution is to be collected;

the organic solvent inlet port is arranged at the lower part of the second reaction vessel and above the aqueous solution collection port; and the aqueous solution inlet port is arranged at the upper part of the second reaction vessel, above the organic solvent inlet port and below the organic solvent collection port. In this apparatus, the aqueous solution supplied through the aqueous solution inlet port flows downward in the second reaction vessel and the organic solvent supplied through the organic solvent inlet port flows upward in the second reaction vessel. As a result, the aqueous solution and the organic solvent flow countercurrently to each other in the second reaction vessel to contact with each other, and the contacted aqueous solution is collected outside the second reaction vessel through the aqueous solution collection port.

In the apparatus, the first reaction vessel (a so-called "reaction vessel") and the second reaction vessel (a so-called "extraction vessel") are in fluid-communication with each other. The silver salt solution collected through the aqueous solution collection port in the first reaction vessel is supplied into the second reaction vessel through the aqueous solution inlet port thereof. It is preferred that the silver salt solution collected through the aqueous solution collection port of the second reaction vessel is refluxed to a aqueous solution inlet port of the first reaction vessel.

Alternatively, the apparatus may be provided with at least one additional reaction vessel that is in fluid-communication with the second reaction vessel. The additional reaction vessel has the same structure as that of the second reaction vessel, and is used for the contact between a silver salt solution collected from the second reaction vessel and a fresh organic solvent. The aqueous solution collected through the aqueous solution collection port of the second reaction vessel is supplied into the additional vessel through the aqueous solution inlet port thereof. It is preferred that the collected silver salt solution that has been subjected to the reaction in the at least one additional reaction vessel is refluxed to the aqueous solution inlet port of the first reaction vessel.

It is preferred that each of the first and second reaction vessels is a vertically long reaction column. It is preferred that, in the first reaction vessel, the difference in height between the raw material solution inlet port and the aqueous solution inlet port is 20 cm or more, preferably from 40 to 300 cm. It is also preferred that, in the second reaction vessel, the difference in height between the organic solvent inlet port and the aqueous solution inlet port is 20 cm or more, preferably from 40 to 300 cm.

It is preferred that the first and second reaction vessels are a closed system, and can prevent oxidation of a PUFA and a silver salt therein.

It is preferred that the apparatus includes a liquid distributor for converting a silver salt solution to be supplied into the first or second reaction vessel into a dispersed phase. Examples of the liquid distributor include a spray nozzle for spraying the silver salt solution into the first or second reaction vessel, a vibrator, a liquid distributor or a porous distribution board which is arranged on a pathway through which the silver salt solution is supplied into the first or second reaction vessel.

It is preferred that the apparatus includes a temperature controller for controlling the temperature of the silver salt solution in the first or second reaction vessel. Examples of the temperature controller include a heater or a cooler for warming or cooling a raw material solution, an organic solvent or a silver salt solution which is not supplied into the first or second reaction vessel yet, and a heater or a cooler for warming or cooling the temperature of the whole of the inside of a reaction vessel. It is preferred that the temperature of a silver salt solution in the first reaction vessel is adjusted to 5 to 30° C. and the temperature of a silver salt solution in the second reaction vessel is adjusted to 30 to 80° C. by the temperature controller.

An embodiment of the apparatus equipped with a pathway through which the silver salt solution is delivered from a first reaction vessel to a second reaction vessel is shown in FIG. 4. The apparatus shown in FIG. 4 is equipped with a first reaction vessel 1 and a second reaction vessel 2. The first reaction vessel 1 is equipped with a raw material solution inlet port 11, a raw material solution collection port 12, an aqueous solution inlet port 13, and an aqueous solution collection port 14. The second reaction vessel 2 is equipped with an organic solvent inlet port 21, an organic solvent collection port 22, an aqueous solution inlet port 23, and an aqueous solution collection port 24. A silver salt solution 100 supplied into the first reaction vessel 1 through the aqueous solution inlet port 13 falls downward in the reaction vessel 1, flows countercurrently with a raw material solution 200, and is collected through the aqueous solution collection port 14 located at a lower part of the reaction vessel 1. The collected silver salt solution 100 is supplied into the second reaction vessel 2 through the aqueous solution inlet port 23, falls downward in the reaction vessel 2, flows countercurrently with an organic solvent 300, and is collected through the aqueous solution collection port 24 located at a lower part of the reaction vessel 2. The silver salt solution 100 collected from the reaction vessel 2 is supplied into the first reaction vessel 1 again through the aqueous solution inlet port 13. The reaction vessels 1 and 2 are equipped with liquid distributors 31 and 32, respectively, for dispersing the silver salt solution 100. Each of the liquid distributors 31 and 32 is in a form of a stacked dispersion board. The apparatus shown in FIG. 4 is also equipped with a condenser 40 for concentrating the organic solvent collected from the reaction vessel 2 to purify a PUFA. The condenser 40 shown in FIG. 4 is a distiller, and the organic solvent 300 is distilled in the distiller. The organic solvent collected from the condenser 40 is returned to the reaction vessel 2 and can be re-used.

Examples of the apparatus having the above-mentioned constitution include a liquid-liquid extraction apparatus disclosed in JP 2004-243203 A. The present invention provides novel use of the apparatus, that is, the application of the apparatus to the production of a PUFA-containing composition through a reaction of a PUFA raw material with a silver salt.

(3.3) Advantages

According to the method for producing a PUFA-containing composition disclosed in this section, a PUFA-containing raw material solution and a silver salt solution can be contacted with each other with high efficiency. Therefore, it is not needed to use a silver salt solution in a large amount for extraction of a PUFA from a raw material, and it is not needed to stir a mixed solution of a raw material solution and a silver salt solution for improving an extraction efficiency. According to this method, it becomes possible to reduce the amount of the silver salt solution necessary for extraction of a PUFA to ½ to 1/20, as compared with the conventional method (stirring-mixing of a raw material solution and a silver salt solution). According to this method, a PUFA-containing silver salt solution thus extracted is separated from other liquids, and therefore it is not needed to halt an extraction operation for the collection of the PUFA-containing silver salt solution and operations for extracting and collecting a PUFA can be carried out continuously. The present invention provides a high-efficient and low-cost PUFA production method.

EXAMPLES

Hereinbelow, the present invention will be described in more detail with reference to examples. However, the present invention is not limited only to these examples.

Test Example 1

Analysis of Fatty Acid Composition in PUFA-containing Composition

Fatty acids analyzed in the following Test Example 1 are as follows: AA-E: an arachidonic acid ester, DPA-E: a docosapentaenoic acid ester, DHA-E: a docosahexaenoic acid ester, ETA-E: an eicosatetraenoic acid ester, and EPA-E: an eicosapentaenoic acid ester.

The method for analyzing a fatty acid compositional ratio was as follows.

A measurement sample in an amount of 12.5 mg was diluted with 1 mL of n-hexane, and analyzed for the content ratio of each of fatty acids in the total fatty acids using a gas chromatography analysis apparatus (Type 7890 GC; Agilent Technologies) under the following conditions. Each of the results was expressed in % by mass which was converted from an area of a chromatogram.
<Conditions for Inlet Port>
Temperature of inlet port: 250° C., split ratio: 10
<Conditions for Column>
Column: DB-WAX manufactured by J&W, 0.25 mm×30 m, column temperature: 210° C.
He flow amount: 1.0 mL/min, He pressure: 20 PSI
<Conditions for Detection>
$H_2$ flow amount: 40 mL/min, Air flow amount: 450 mL/min
He flow amount: 1.00 mL/min, DET temperature: 260° C.

The methods for calculating an AA-E/EPA-E area percentage ratio and an ETA-E/EPA-E area percentage ratio are as follows.

$$AA\text{-}E/EPA\text{-}E \text{ area percentage ratio } (\%) = \frac{\text{mass of } AA\text{-}E \text{ in product}}{\text{mass of } EPA\text{-}E \text{ in product}} \times 100$$

$$ETA\text{-}E/EPA\text{-}E \text{ area percentage ratio } (\%) = \frac{\text{mass of } ETA\text{-}E \text{ in product}}{\text{mass of } EPA\text{-}E \text{ in product}} \times 100$$

The methods for calculating an EPA-E area percentage value, a DHA-E area percentage value and a DPA-E area percentage value are as follows.

$$EPA\text{-}E \text{ area percentage value } (\%) = \frac{\text{mass of } EPA\text{-}E \text{ in product}}{\text{mass of product}} \times 100$$

$$DHA\text{-}E \text{ area percentage value } (\%) = \frac{\text{mass of } DHA\text{-}E \text{ in product}}{\text{mass of product}} \times 100$$

$$DPA\text{-}E \text{ area percentage value } (\%) = \frac{\text{mass of } DPA\text{-}E \text{ in product}}{\text{mass of product}} \times 100$$

The methods for calculating an oil collection rate and an EPA-E collection rate are as follows.

$$\text{Oil collection rate } (\%) = \frac{\text{mass of product}}{\text{mass of raw material}} \times 100$$

$$EPA\text{-}E \text{ collection rate } (\%) = \frac{(\text{mass of } EPA\text{-}E \text{ in product } (\%)) \times (\text{mass of product})}{(\text{mass of } EPA\text{-}E \text{ in raw material}(\%)) \times (\text{mass of raw material})} \times 100$$

Example 1

Five grams of a raw material oil and 2.7 mL of cyclohexane were fully mixed and dissolved, and the resultant mixture was filled in a column (inner diameter: 10 mm, length: 28 cm) (height of the raw material oil solution: 9.5 cm). Twenty grams of an aqueous solution containing 50% by mass of silver nitrate was added dropwise at a flow amount of 2 g/min from the tip of a nozzle chip having an inner diameter of about 1 mm over the raw material oil solution. Concurrently with this procedure, an aqueous phase accumulated at the bottom of the column was collected at a flow amount of 2 g/min so that the height of the raw material oil solution filled in the column could be kept at 9.5 cm. The collected aqueous phase was warmed to 60° C., then 23.3 mL of cyclohexane was added thereto, and then the resultant mixture was stirred at a speed of 300 rpm under the condition of 60° C. for 30 minutes to extract a fatty acid ethyl ester in the aqueous phase into an organic phase. The liquid after the stirring was allowed to stand still, and then the separated organic phase was collected and concentrated, to thereby obtain a fatty acid ethyl ester-containing composition.

Example 2

The same procedure as in Example 1 was carried out, except that the aqueous silver nitrate solution to be added dropwise to a raw material oil solution was made more fine using a vibrator. In this manner, a fatty acid ethyl ester-containing composition was produced.

Example 3

Ten grams of a raw material oil and 5.4 mL of cyclohexane were fully mixed and dissolved, and the resultant mixture was filled in a column A (inner diameter: 6.75 mm, length: 48 cm) (height of the raw material oil solution: 116 cm). Four grams of an aqueous solution containing 50% by mass of silver nitrate was added dropwise at a flow amount of 1 g/min from the tip of a nozzle chip having an inner diameter of about 1 mm over the raw material oil solution while making the aqueous solution more fine using a vibrator. Concurrently with this procedure, an aqueous phase accumulated at the bottom of the column A was collected at a flow amount of 1 g/min so that the height of the raw material oil solution filled in the column A could be kept at 116 cm. Subsequently, the collected aqueous phase was injected from an upper part of a column B (having the same size as that of the column A) while injecting cyclohexane at 60° C. from a lower part of the column B to extract a fatty acid ethyl ester in the aqueous phase into an organic phase. The aqueous silver nitrate solution after the extraction of the fatty acid ethyl ester was collected from a lower part of the column B and was then returned to the column A again. In this manner, the aqueous silver nitrate solution was used repeatedly (4 g of the aqueous silver nitrate solution was passed through the raw material oil solution 2.5 times, and was injected continuously for 10 minutes; that is, the aqueous silver nitrate solution in the total amount of 10 g was contacted with the raw material oil solution). The organic phase into which the fatty acid ethyl ester had been extracted was collected from an upper part of the column B and was then concentrated, to thereby obtain a fatty acid ethyl ester-containing composition.

Example 4

Fifty grams of a raw material oil and 23.3 mL of cyclohexane were fully mixed and dissolved, and the resultant mixture was filled in a column A (inner diameter: 9.4 mm, length: 130 cm) (height of the raw material oil solution: 116 cm). Twenty grams of an aqueous solution containing 50% by mass of silver nitrate was added dropwise at a flow amount of 1 g/min through the tip of a nozzle chip having an inner diameter of about 1 mm over the raw material oil solution while making the aqueous solution more fine using a vibrator. Concurrently with this procedure, an aqueous phase accumulated at the bottom of the column A was collected at a flow amount of 1 g/min so that the height of the raw material oil solution filled in the column A could be kept at 116 cm. Subsequently, the collected aqueous phase was injected from an upper part of a column B (having the same size as that of the column A) while injecting cyclohexane at 60° C. from a lower part of the column B to extract a fatty acid ethyl ester in the aqueous phase into an organic phase. The aqueous silver nitrate solution after the extraction of the fatty acid ethyl ester was collected from a lower part of the column B and was then returned to the column A again. In this manner, the aqueous silver nitrate solution was used repeatedly (20 g of the aqueous silver nitrate solution was passed through a raw material oil solution 2.5 times, and was injected continuously for 50 minutes; that is, the aqueous silver nitrate solution in the total amount of 50 g was contacted with). The organic phase into which the fatty acid ethyl ester had been extracted was collected from an upper part of the column B and was then concentrated, to thereby obtain a fatty acid ethyl ester-containing composition.

Example 5

The same procedure as in Example 4 was carried out to produce a fatty acid ethyl ester-containing composition. In the procedure, 20 g of an aqueous silver nitrate solution was passed through a raw material oil solution 10 times and was injected continuously for 200 minutes; that is, the aqueous silver nitrate solution in the total amount of 200 g was contacted with the raw material oil solution Comparative Example 1

Fifty grams of a raw material oil and 23.3 mL of cyclohexane were fully mixed and dissolved. Two hundreds grams of an aqueous solution containing 50% by mass of silver nitrate was added to the solution, and the resultant mixture was stirred at a speed of 450 rpm under the condition of 20° C. for 40 minutes. A solution obtained after the stirring was allowed to stand still, then the separated organic phase was removed and an aqueous phase was collected. The aqueous phase was warmed to 60° C., 233 mL of cyclohexane was added thereto, and the resultant solution was stirred at a speed of 300 rpm under the condition of 60° C. for 30 minutes to extract a fatty acid ethyl ester in the aqueous phase into an organic phase. A solution obtained after the stirring was allowed to stand still, and then the separated organic phase was collected and concentrated, to thereby produce a fatty acid ethyl ester-containing composition.

The compositional ratio of each fatty acid relative to the total fatty acids, the oil collection rate and the EPA collection rate in each of the compositions produced in Examples 1 to 5 and Comparative Example 1 were determined. As shown in Table 1, the oil collection rate and the EPA-E collection rate were improved by increasing the passing frequency of the aqueous silver nitrate solution through the raw material oil solution or the retention time of retention of the aqueous silver nitrate solution in the raw material oil solution or by making the aqueous silver nitrate solution more fine. Furthermore, as shown in Table 2, in Example 5 where the retention time was long, the area percentage ratio of each of an AA-E and an ETA-B relative to an EPA-E were decreased and the EPA-E collection rate and the oil collection rate were also improved, as compared with those in Comparative Example 1 (the conventional method employing mixing by stirring), in spite of a fact that the amount of the aqueous silver nitrate solution used was reduced to 1/10. When an aqueous silver nitrate solution is used repeatedly through dropwise addition and collection, it becomes possible to achieve a high oil collection rate and a high EPA collection rate even if the aqueous silver nitrate solution is used in a small amount. In the conventional method employed in Comparative Example 1, it was confirmed that the collection of the fatty acid was completed within a retention time of 40 minutes and the collection rate was not improved any more even when the retention time was prolonged.

TABLE 1

|  | Raw material oil | Example 1 | Example 2 | Example 3 | Example 4 | Example 5 |
| --- | --- | --- | --- | --- | --- | --- |
| Column inner diameter (mm) |  | 10 | 10 | 6.75 | 9.4 | 9.4 |
| Charged continuous phase (mL)*1 |  | 8.2 | 8.2 | 16.4 | 78.2 | 78.2 |
| Height of dropwise addition (cm)*2 |  | 9.5 | 9.5 | 46 | 116 | 116 |
| Making aqueous silver solution more fine |  | No | Yes (vibration) | Yes (vibration) | Yes (vibration) | Yes (vibration) |
| Amount of aqueous silver solution used (g/1 g of raw material oil solution) |  | 4 | 4 | 0.4 | 0.4 | 0.4 |
| Flow rate (g/min) |  | 2 | 2 | 1 | 1 | 1 |

TABLE 1-continued

|  | Raw material oil | Example 1 | Example 2 | Example 3 | Example 4 | Example 5 |
|---|---|---|---|---|---|---|
| Number of repeats |  | 1 | 1 | 2.5 | 2.5 | 10 |
| Contact amount (g/1 g of raw material oil solution) |  | 4 | 4 | 1 | 1 | 4 |
| Retention time (min) |  | 10 | 10 | 10 | 50 | 200 |
| Fatty acid compositional ratio |  |  |  |  |  |  |
| AA-E/EPA-E area percentage ratio | 5.55 | 0.91 | 0.70 | 0.13 | 0.12 | 0.16 |
| ETA-E/EPA-E area percentage ratio | 3.86 | 0.78 | 0.78 | 0.19 | 0.18 | 0.26 |
| Fatty acid composition |  |  |  |  |  |  |
| EPA-E area percentage value | 44.64 | 68.36 | 69.94 | 68.52 | 68.35 | 77.03 |
| DHA-E area percentage value | 7.46 | 16.42 | 17.98 | 26.16 | 26.58 | 16.19 |
| Oil collection rate |  | 22.2 | 25.4 | 8.70 | 12.38 | 42.8 |
| EPA-E collection rate |  | 34.1 | 39.9 | 13.4 | 19.0 | 73.9 |

*[1]Oil:cyclohexane ≈ 2:1 (v/v) (specific gravity of oil: 0.91)
*[2]Height of dropwise addition ≈ (height of continuous phase (raw material oil solution)) − (length of immersed part of dropping nozzle)

TABLE 2

|  | Example 5 | Comparative Example 1 |
|---|---|---|
| Column inner diameter (mm) | 9.4 | — |
| Charged continuous phase (mL)*[1] | 78.2 | 78.2 |
| Height of dropwise addition (cm)*[2] | 116 | — |
| Making aqueous silver solution more fine | Yes (vibration) | No (stirring) |
| Amount of aqueous silver solution used (g/1 g of raw material oil solution) | 0.4 | 4 |
| Flow rate (g/min) | 1 | — |
| Number of repeats | 10 | 0 |
| Contact amount (g/1 g of raw material oil solution) | 4 | 4 |
| Retention time (min) | 200 | 40 |
| Fatty acid compositional ratio |  |  |
| AA-E/EPA-E area percentage ratio | 0.16 | 0.25 |
| ETA-E/EPA-E area percentage ratio | 0.26 | 0.39 |
| Fatty acid composition |  |  |
| EPA-E area percentage value | 77.03 | 76.36 |
| DHA-E area percentage value | 16.19 | 15.50 |
| Oil collection rate | 42.8 | 40.0 |
| EPA-E collection rate | 73.9 | 68.6 |

*[1]Oil:cyclohexane ≈ 2:1 (v/v) (specific gravity of oil: 0.91)
*[2]Height of dropwise addition ≈ (height of continuous phase (raw material oil solution)) − (length of immersed part of dropping nozzle)

Example 6

Fifty grams of a raw material oil and 23.3 mL of cyclohexane were fully mixed and dissolved, and the resultant mixture was filled in a column (inner diameter: 9.4 mm, length: 130 cm) (height of the raw material oil solution: 116 cm). Ten grams of an aqueous solution containing 50% by mass of silver nitrate was added dropwise at a flow amount of 2 g/min through the tip of a nozzle chip having an inner diameter of about 1 mm over the raw material oil solution while making the aqueous solution more fine using a vibrator. Concurrently with this procedure, an aqueous phase accumulated at the bottom of the column was collected at a flow amount of 2 g/min so that the height of the raw material oil solution filled in the column could be kept at 116 cm. The collected aqueous phase was warmed to 60° C., then 11.7 mL of cyclohexane was added thereto to extract a fatty acid ethyl ester in the aqueous phase into an organic phase, and then the organic phase was fractionated and concentrated. In this manner, a fatty acid ethyl ester-containing composition and 10 g of a 50%-by-mass aqueous silver nitrate solution were obtained.

Subsequently, 2 mL of the raw material oil solution in the column was removed, and a fresh raw material oil solution was supplemented so that the height of the raw material oil solution in the column could be 116 cm. Into the resultant solution, 10 g of the aqueous silver nitrate solution separated from the fatty acid ethyl ester was added dropwise. The separation of a fatty acid ethyl ester-containing composition was carried out in the same manner as mentioned above. This procedure was repeated 50 times, and then the composition of the collected fatty acid ethyl ester-containing composition was analyzed.

Example 7

A raw material oil in an amount of 71.4 g was filled in a column (inner diameter: 10.0 mm, length: 126 cm) (height of the raw material oil solution: 100 cm). Fifty grams of an aqueous solution containing 50% by mass of silver nitrate was added dropwise at a flow amount of 3.5 g/min through the tip of a nozzle chip having an inner diameter of about 1 mm over the raw material oil solution while making the solution more fine using a vibrator. Concurrently with this procedure, an aqueous phase accumulated at the bottom of the column was collected at a flow amount of 3.5 g/min, and the raw material oil was removed at a flow rate of 1.5 g/min from an upper part of the column while injecting a fresh raw material oil at a flow rate of 1.5 g/min from a lower part of the column. In this manner, the height of the raw material oil filled in the column could be kept at 100 cm. The collected aqueous phase was warmed to 60° C., then 233.3 mL of cyclohexane was added thereto to extract a fatty acid ethyl ester in the aqueous phase into an organic phase, and then the organic phase was fractionated and concentrated. In this manner, a fatty acid ethyl ester-containing composition and 50 g of a 50%-by-mass aqueous silver nitrate solution were obtained. The 50 g of the aqueous silver nitrate solution thus obtained was returned to the column, and the separation of the fatty acid ethyl ester-containing composition was repeated 7 times in the same manner as mentioned above. The composition of the collected fatty acid ethyl ester-containing composition was analyzed.

Figure 5B:
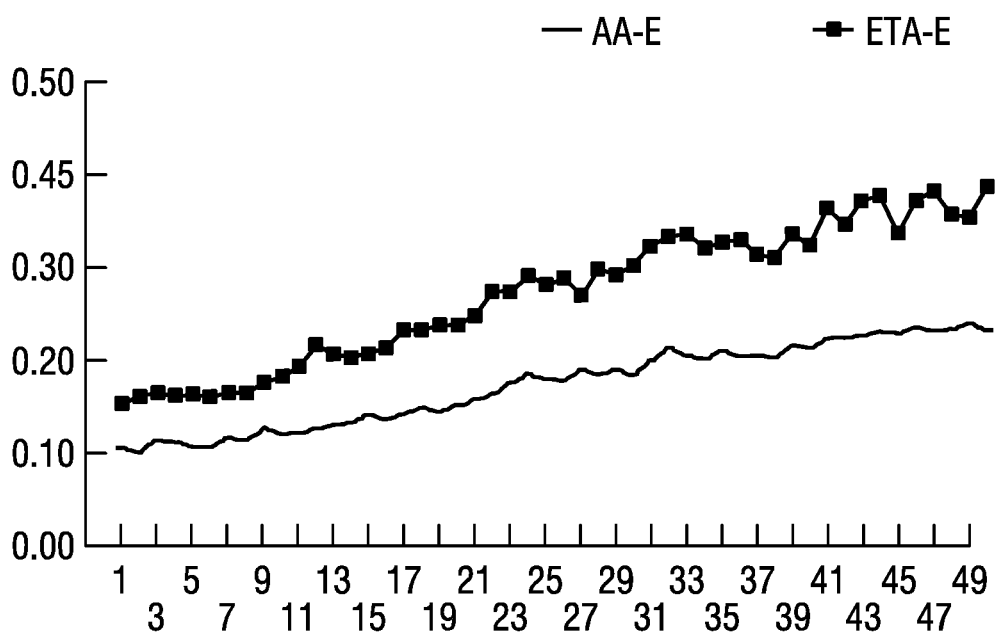

The results of the fatty acid composition analysis of each of the fatty acid ethyl ester-containing compositions obtained in Examples 6 and 7 are shown in Table 3. The variations of fatty acid composition with repeated use of the aqueous silver nitrate solution in the fatty acid ethyl ester-containing compositions of Examples 6 and 7 are shown in FIGS. 5 and 6, respectively. The compositional ratios of EPA-E and DHA-E in the fatty acid ethyl ester-containing composition tended to become constant while the compositional ratios of AA-E and ETA-E there tended to be increased with the repeat of the operation.

TABLE 3

|  | Example 6 | Example 7 |
|---|---|---|
| Column inner diameter (mm) | 9.4 | 10 |
| Charged continuous phase (mL)*1 | 78.2 | 78.5 |
| Height of dropwise addition (cm)*2 | 116 | 100 |
| Making aqueous silver solution more fine | Yes (vibration) | Yes (vibration) |
| Amount of aqueous silver solution used (g/1 g of raw material oil solution) | 0.066 | 0.22 |
| Flow rate (g/min) | 2 | 3.5 |
| Number of repeats | 50 | 7 |
| Contact amount (g/1 g of raw material oil solution) | 3.3 | 1.5 |
| Retention time (min) | 250 | 100 |
| Fatty acid composition |  |  |
| AA-E/EPA-E area percentage ratio | 0.23 | 0.22 |
| ETA-E/EPA-E area percentage ratio | 0.39 | 0.32 |
| EPA-E area percentage value | 77.37 | 71.30 |
| DHA-E area percentage value | 14.13 | 22.09 |
| Oil collection rate | 12.0 | 19.8 |
| EPA-E collection rate | 20.6 | 31.1 |

*1Oil:cyclohexane ≈ 2:1 (v/v) (specific gravity of oil: 0.91)
*2Height of dropwise addition ≈ (height of continuous phase (raw material oil solution)) − (length of immersed part of dropping nozzle)

Test Example 2

Evaluation of Level of Deterioration of Silver Salt Solution

Reference Example 1

Analysis of Compositional Ratio of Fatty Acids

A measurement sample in an amount of 12.5 mg was diluted with 1 mL of n-hexane, and the resultant solution was analyzed for the content ratio of each of fatty acids r in the total fatty acids using a gas chromatography analysis apparatus (Type 7890 GC; manufactured by Agilent Technologies) under the following conditions. The results are expressed in % by mass each converted from the area of a chromatogram.

<Conditions for Inlet Port>
Temperature of inlet port: 250° C., split ratio: 10
<Conditions for Column>
Column: DB-WAX manufactured by J&W, 0.25 mm×30 m, column
  temperature: 210° C.
He flow amount: 1.0 mL/min, He pressure: 20 PSI
<Conditions for Detection>
$H_2$ flow amount: 40 mL/min, air flow amount: 450 mL/min
He flow amount: 1.00 mL/min, DET temperature: 260° C.
The analyzed fatty acids are as follows: AA-E: arachidonic acid ethyl ester, DPA-E: docosapentaenoic acid ethyl ester, DHA-E: docosahexaenoic acid ethyl ester, ETA-E: eicosatetraenoic acid ethyl ester, and EPA-E: eicosapentaenoic acid ethyl ester.

Reference Example 2

Method for Measuring Free Fatty Acid Content in Silver Salt Solution

1. Preparation of Standard Solution
    (1) Myristic acid in an amount of 0.114 g was placed in a 100-mL measuring flask, and was then diluted with dimethyl sulfoxide to 100 mL.
    (2) Triethanolamine in an amount of 1.5 g was separately placed in a 100-mL measuring flask, and was then diluted with pure water to 100 mL.
    (3) Eethylenediaminetetraacetic acid tetrasodium salt tetrahydrate in an amount of 0.10 g was placed in a 100-mL measuring flask, and was then diluted with pure water to 100 mL.
    (4) The solution prepared in (1) in an amount of 20 mL, the solution prepared in (2) in an amount of 10 mL and the solution prepared in (3) in an amount of 10 mL were placed in a 100-mL measuring flask, and were then diluted with pure water to 100 mL to produce a standard solution.
2. Preparation of Copper Sample Solution
    (1) Copper (II) sulfate pentahydrate in an amount of 6.49 g and sodium chloride in an amount of 20.0 g were placed in a beaker and were then dissolved in pure water, then the resultant solution was transferred to a 100-mL measuring flask and was then combined with a wash solution of the beaker, and then the resultant solution was diluted with pure water to 100 mL.
    (2) Separately, triethanolamine in an amount of 14.9 g was separately placed a 100-mL measuring flask, and was then diluted with pure water to 100 mL.
    (3) The same amounts (by volume) of the solution prepared in (1) and the solution produced in (2) were mixed together to prepare a copper sample solution.
3. Preparation of Color-developing Sample Solution
    Bathocuproine in an amount of 0.189 g was placed in a 250-mL measuring flask, and was then diluted with 2-butanol to 250 mL.
4. Operational Procedure
    (1) Each of a silver salt solution in an amount of 5 µL and the standard solution in an amount of 500 µL was placed in a capped test tube, and then 1 mL of the copper sample solution was added thereto.
    (2) A chloroform/heptane mixed solution (1/1 by volume) in an amount of 3 mL was added to each of the test tubes, and each of the test tubes was capped and was then shaken vigorously with a hand for 3 minutes.
    (3) After the shaking, the cap was removed from each of the test tubes, and then the test tubes were centrifuged (3,000 rpm).
    (4) A supernatant in an amount of 2 mL was collected and was placed in another test tube, then the color-developing sample solution in an amount of 2 mL was added to the test tube, and then the resultant solution was shaken gently.
    (5) Two to three minutes after, an absorbance at 475 nm was measured using pure water as a control.
5. Calculation Formula
    The concentration of a free fatty acid in an aqueous silver solution was calculated in accordance with the following formula (1).

$$\text{Concentration of free fatty acid (meq}/L) = (B/A) \times (D/C) \qquad \text{(Formula 1)}$$

A: An absorbance obtained using standard solution
B: An absorbance obtained using a sample solution
C: An amount of a sample collected (μL)
D: An amount of the standard solution collected (μL)
(Materials)
Raw material oils: AA-E 2.6%, ETA-E 1.7%, EPA-E 44.5%, DPA-E 2.1%, DHA-E 7.4%,
Peroxide value (POV)=1.0 mEq/kg,
Acid value (AV)=0.1 mg/g
Silver salt solution: a 50%-by-mass aqueous silver nitrate solution
Organic solvent: cyclohexane
Reaction vessel, extraction vessel:
Example 8; column (inner diameter: 20 mm, length: 20 cm, a cylinder-like form)
The position of the tip of a silver salt solution inlet port (nozzle, inner diameter: about 1 mm) was within 2 cm below the upper surface of a continuous organic phase (a raw material solution, an organic solvent), and the position of a silver salt solution collection port was a lower part of the column.
Example 9; a glass tube (inner diameter: 3 mm, length: 45 cm, a cylinder-like form)
A metal mesh was filled in the tube.

Example 8

A PUFA ethyl ester was purified from the raw material oil by a continuous-mode utilizing countercurrent flows. Thirty grams of the raw material oil was mixed with 14 mL of an organic solvent, and dissolved to prepare a raw material solution. The raw material solution in an amount of 47 mL was filled in a first column (a reaction vessel), and then an argon gas was blown from an upper part of the column to purge air in the column (the oxygen concentration in the column: 0.1% or less). A silver salt solution in an amount of 120 g was added dropwise through an inlet port in the column at a flow amount of 10 g/min to contact the raw material solution with the silver salt solution. The silver salt solution to be added dropwise was made more fine using a vibrator. Concurrently with the dropwise addition of the silver salt solution, an aqueous phase accumulated at the bottom of the column was collected at a rate of 11 g/min. The distance between the nozzle tip of the inlet port of the column and the upper surface of the aqueous phase was kept at 13 cm. Subsequently, the aqueous phase collected from the first column (a silver salt solution containing a PUFA ethyl ester) was added dropwise to a second column (an extraction vessel; an argon gas was blown into the column to purge air) filled with an organic solvent having a temperature of 60° C. through the inlet port of the column at a flow amount of 11 g/min to contact the aqueous phase with the organic solvent, thereby extracting the PUFA ethyl ester in the aqueous phase into the organic phase. Concurrently with the dropwise addition of the aqueous phase, the silver salt solution accumulated at the bottom of the second column was collected at a flow amount of 10 g/min. The distance between the nozzle tip of the inlet port of the second column and the upper surface of the aqueous phase was kept at 13 cm. The organic phase was separated from the second column, then collected and concentrated to obtain a PUFA ethyl ester-containing composition. A portion of the aqueous phase (silver salt solution) collected from the second column was subjected to the measurement of the free fatty acid content, and the remainder was re-used. A series of steps as mentioned above was defined as one process, and the process was repeated, and deterioration of the silver salt solution over time on the basis of the free fatty acid content during the repeated use was observed. Each of the raw material solution in the first column and the organic solvent in the second column was replaced by a fresh one in every process.

Example 9

A PUFA ethyl ester was purified from the raw material oil in a continuous-mode utilizing parallel flows. Thirty grams of the raw material oil was mixed with 14 mL of an organic solvent, and dissolved to prepare a raw material solution. The obtained raw material solution and a silver salt solution flowed into a first glass tube (reaction vessel) in parallel through one end (inlet port) thereof to contact these solutions with each other. The silver salt solution in an amount of 120 g was flowed into the glass tube at a flow amount of 30 g/min, and the raw material solution in an amount of 41 g was flowed into the glass tube at a flow amount of 10.3 g/min.
The silver salt solution and the raw material solution were pressed into the reaction vessel using a glass tube that was connected to the inlet port and had an inner diameter of 5.5 mm. The end (collection port) located on the opposite side of the first glass tube was directly connected to a distribution vessel (column), and an aqueous phase (a silver salt solution containing a PUFA ethyl ester solution) accumulated at the bottom of the distribution vessel was pressed into the second glass tube (extraction vessel) through one end thereof at a flow amount of 33 g/min. Concurrently with this procedure, 140 mL of an organic solvent was flowed from the same end of the second glass tube at a flow amount of 35 mL/min to contact the aqueous phase with the organic solvent, thereby extracting the PUFA ethyl ester in the aqueous phase. The end (collection port) located on the opposite side of the second glass tube was directly connected to a second distribution vessel (column), and an aqueous phase (a silver salt solution) accumulated at the bottom of the distribution vessel was separated from the organic phase and was collected. An organic solvent was distilled away from the organic phase to obtain a PUFA ethyl ester-containing composition. A portion of an aqueous phase (silver salt solution) collected from the second distribution vessel was subjected to the measurement of a free fatty acid content, and the remainder was re-used. A series of steps as mentioned above was defined as one process, the process was repeated, and deterioration of the silver salt solution over time on the basis of the free fatty acid content during the repeated use was observed. The raw material solution and the organic solvent were replaced by a fresh one in every process.

Comparative Example 2

A PUFA ethyl ester was purified from the raw material oil in a batch-mode. Thirty grams of the raw material oil was well mixed with 14 mL of an organic solvent, and dissolved to obtain a raw material solution. A silver salt solution in an amount of 120 g and the raw material solution in an amount of 41 g were introduced into a flask, and the resultant solution was stirred at 20° C. for 20 minutes at a speed of 300 rpm under a nitrogen atmosphere (oxygen concentration: 0.4%). A solution obtained after the stirring was allowed to stand still at 20° C. for 15 minutes, then a separated organic phase was removed, and then an aqueous phase (a silver salt solution containing a PUFA ethyl ester) was collected. The aqueous phase thus obtained was warmed to 60° C., then 140 mL of an organic solvent was added thereto, the resultant solution was stirred at a speed of 300 rpm under the condition of 60° C. for 20 minutes, and a PUPA ethyl ester in an aqueous phase was extracted into an organic phase. A liquid obtained after the stirring was allowed to stand still, and then a separated organic phase was collected and concentrated to obtain a PUFA ethyl ester-containing composition. The aqueous phase (silver salt solution) that was left was collected, and a portion thereof was subjected to the measurement of a free fatty acid content, and the remainder was re-used. A series of steps as mentioned above was defined as one process, and the process was repeated, and deterioration of the silver salt solution over time on the basis of the free fatty acid content during the repeated use was observed. The raw material solution and the organic solvent was replaced by a fresh one in every process.

Comparative Example 3

The same procedure as in Comparative Example 2 was carried out on a scale 5,000 times greater than that in Comparative Example 1. The conditions, including the time of stirring, the rate of stirring and the temperature, were substantially the same as those employed in Comparative Example 2.

Test Example 2-1

Comparison of Silver Salt Solution Deterioration Levels (Free Fatty Acid Contents)

The change over time in free fatty acid (FFA) content in each of the products produced in Example 8, Example 9 and Comparative Example 2 with an increase in the number of repeated uses of the silver salt solution (the number of processes) is shown in FIG. 7.

Test Example 2-2

Relationship Between Time of Treatment and Deterioration of Silver Salt Solution The PUFA contact time of a silver salt solution in each process and the average value of increases in FFA contents (an average for 10 processes) in Example 8, Example 9, Comparative Example 2 and Comparative Example 3 are shown in Table 4. PUFA contact time of a silver salt solution is a time during which a complex of a PUFA ethyl ester and a silver ion is present in the silver salt solution (that is, a time period between a time point at which the silver salt solution is supplied to a raw material solution and a time point at which a PUFA ethyl ester-containing composition is extracted from the silver salt solution with an organic solvent). In other words, it is the sum of a time of contact between the silver salt solution and the raw material solution in the reaction vessel, a time of standing still the silver salt solution in the reaction vessel or a distribution vessel after the contact, a time of transferring to an extraction vessel and a time of contact between the silver salt solution and an organic solvent in the extraction vessel.

TABLE 4

PUFA contact time and FFA increase in silver salt solution per process (average value for 10 processes)

| | Reaction vessel | | Extraction | | | |
|---|---|---|---|---|---|---|
| | Raw material solution contact time | Standing still time after contact *[1] | Transferring time | vessel Organic solvent contact time | Average total contact time | Average FFA increase |
| Example 8 | 5-60 sec | 250 sec | 10 sec | 5-60 sec | 4-6 min | 0.13 |
| Example 9 | 5-20 sec | 250 sec | 10 sec | 5-20 sec | 4-5 min | 0.13 |
| Comparative Example 2 | 20 min | 15 min | 5 min | 20 min | 60 min | 1.21 |
| Comparative Example 3 | 40 min | 25 min | 25 min | 40 min | 130 min | 10.87 |

*[1] Retention time at lower part of column (Example 8) or retention time in distribution vessel (Example 9)

As shown in Table 4, an FFA content in a silver salt solution increased with the increase in the PUFA contact time. In Examples 8 and 9 where a continuous-mode was employed, the PUFA contact time of a silver salt solution was shorter and an increase in FFA content was smaller, as compared with Comparative Examples 2 and 3 where a batch-mode was employed. From these results, it was demonstrated that the deterioration of a silver salt solution was inhibited in Examples 8 and 9.

Test Example 2-3

Relationship Between Amount of Silver Salt Solution Used and Yield of PUFA

The total yield of a PUFA-containing composition which was obtained until the FFA content in a silver salt solution exceeded 10 mEq/L or 50 mEq/L in Example 8, Example 9, Comparative Example 2 and Comparative Example 3 is shown in Table 5. In Examples 8 and 9 where a continuous mode was employed, the yield of a PUFA-containing composition was increased to 8 times or more when the FFA content in the silver salt solution became 10 mEq/L, and also increased to 25 times or more when the FFA content in the silver salt solution became 50 mEq/L, as compared with Comparative Examples 2 and 3 where a batch mode was employed. From these results, it was demonstrated that, in Examples 8 and 9, the amount of the silver salt solution which was required for the production of a PUFA-containing composition could be decreased significantly, as compared with cases where a batch mode was employed.

TABLE 5

|  | Total amount of silver salt solution used | FFA content exceeds 10 mEq/L | | FFA content exceeds 50 mEq/L | |
|---|---|---|---|---|---|
|  |  | Number of processes | Yield of PUFA-containing composition | Number of processes | Yield of PUFA-containing composition |
| Example 8 | 120 g | 78 rounds | 1240 g | No data | No data |
| Example 9 | 120 g | 76 rounds | 1208 g | 384 rounds | 6106 g |
| Comparative Example 2 | 120 g | 9 rounds | 143 g | 15 rounds | 238 g |
| Comparative Example 3 | 150 kg | 2 rounds | 80 kg | 4 rounds | 159 kg |

Test Example 2-4

Deterioration (Change in Color) of Silver Salt Solution

The appearance and color (a Gardner color scale) of the silver salt solution that was used repeatedly 30 times in Example 9 were compared with those in Comparative Example 3. A Gardner color scale of the solution was evaluated by carrying out a sensory test in which the solution was compared with a Gardner standard solution with naked eyes by three persons and an average of the results was taken. The results are shown in Table 6.

TABLE 6

|  | Appearance | Gardner color scale |
|---|---|---|
| Example 9 | Yellow | 5 |
| Comparative Example 3 | Reddish brown | 14 |

Test Example 2-5

Relationship Between POV of Raw Material Solution and Deterioration of Silver Salt Solution The influence of the oxidative deterioration of a raw material oil on deterioration of the silver salt solution was examined. A PUFA ethyl ester was purified in the same procedure as in Example 8 or 9 using the below-mentioned raw material oils A to F that had different oxidation indexes (POVs and AVs) from one another. The purification of the PUFA ethyl ester was also carried out according to the procedure in Comparative Example 2 using the below-mentioned raw material oils E to F. The change in FFA content in the silver salt solution after the silver salt solution was used repeatedly three times (3 processes) was determined. The results are shown in Table 7.

Raw material oil A: POV=1.0 mEq/kg, AV=0.1 mg/g
Raw material oil B: POV=1.0 mEq/kg, AV=0.2 mg/g
Raw material oil C: POV=5.2 mEq/kg, AV=0.2 mg
Raw material oil D: POV=11.6 mEq/kg, AV=0.1 mg
Raw material oil E: POV=40.5 mEq/kg, AV=0.2 mg
Raw material oil F: POV=1.3 mEq/kg, AV=5.3 mg (In all of these raw material oils, the fatty acid composition was as follows: AA-E 2.8%, ETA-E 1.8%, EPA-B 44.7%, DPA-E 2.0%, and DHA-E 7.7%.)

TABLE 7

| Purification method | Raw material oil | POV (mEq/kg) | AV (mg/g) | FFA content in silver salt solution (mEq/L) | |
|---|---|---|---|---|---|
|  |  |  |  | Before use (0 process) | Used 3 times (after 3 processes) |
| Example 8 | A | 1.0 | 0.1 | 0.1 | 0.7 |
| Example 9 | B | 1.0 | 0.2 | 0.2 | 1.0 |
| Example 8 | C | 5.2 | 0.2 | 0.4 | 1.9 |
|  | D | 11.6 | 0.1 | 0.3 | 4.0 |
|  | E | 40.5 | 0.2 | 0.0 | 6.4 |
|  | F | 1.3 | 5.3 | 0.0 | 12.0 |
| Comparative Example 2 | E | 40.5 | 0.2 | 0.0 | 58.6 |
|  | F | 1.3 | 5.3 | 0.0 | 25.0 |

REFERENCE SIGNS LIST

1: First reaction vessel
2: Second reaction vessel
11: Raw material solution inlet port
12: Raw material solution collection port
13: Aqueous solution inlet port
14: Aqueous solution collection port
21: Organic solvent inlet port
22: Organic solvent collection port
23: Aqueous solution inlet port
24: Aqueous solution collection port
31, 32: Liquid distributor
40: Condenser
100: Silver salt solution
200: Raw material solution
300: Organic solvent

The invention claimed is:
1. A method for producing a composition comprising a polyunsaturated fatty acid, comprising:
   supplying an aqueous solution comprising a silver salt into a reaction vessel to contact the aqueous solution with a raw material solution comprising an alkyl ester of the polyunsaturated fatty acid, wherein the aqueous solution comprising the silver salt exists in a form of a dispersed phase and the raw material solution comprising an alkyl ester of the polyunsaturated fatty acid exists in a form of a continuous phase: and
   collecting the aqueous solution comprising the silver salt which has been contacted with the raw material solution from the reaction vessel,
   wherein the supply of the aqueous solution comprising the silver salt into the reaction vessel and the collection of the aqueous solution comprising the silver salt from the reaction vessel are carried out concurrently with each other.

2. The method according to claim 1, wherein the supply of the aqueous solution comprising the silver salt into the reaction vessel, the contact of the aqueous solution comprising the silver salt with the raw material solution, and the collection of the aqueous solution comprising the silver salt from the reaction vessel are carried out under a low oxygen condition.

3. The method according to claim 1, wherein the raw material solution comprising an alkyl ester of the polyunsaturated fatty acid has such an oxidation index that a POV is 10 or less or an AV is 0.3 or less.

4. The method according to claim 1, wherein the polyunsaturated fatty acid comprises eicosapentaenoic acid or docosahexaenoic acid.

5. The method according to claim 1, further comprising:
supplying the aqueous solution comprising a silver salt which has been collected from the reaction vessel into an extraction vessel to contact the aqueous solution comprising the silver salt with an organic solvent; and
collecting the contacted aqueous solution comprising the silver salt from the extraction vessel,
wherein the supply of the aqueous solution comprising the silver salt into the extraction vessel and the collection of the aqueous solution comprising the silver salt from the extraction vessel are carried out concurrently with each other.

6. The method according to claim 5, further comprising supplying the aqueous solution comprising the silver salt which is collected from the extraction vessel into the reaction vessel again.

7. The method according to claim 5, wherein the supply of the aqueous solution comprising the silver salt into the extraction vessel, the contact of the aqueous solution comprising the silver salt with the organic solvent and the collection of the aqueous solution comprising the silver salt from the extraction vessel are carried out under a low oxygen condition.

8. The method according to claim 5, wherein in the extraction vessel,
the aqueous solution comprising the silver salt exists in a form of a dispersed phase and the organic solvent exists in a form of a continuous phase, or
the aqueous solution comprising the silver salt exists in a form of a continuous phase and the organic solvent exists in a form of a dispersed phase.

9. The method according to claim 5, wherein the organic solvent is hexane or cyclohexane.

10. A method for producing a composition comprising a polyunsaturated fatty acid, comprising:
supplying an aqueous solution comprising a silver salt into a raw material solution comprising an alkyl ester of the polyunsaturated fatty acid such that the aqueous solution comprising the silver salt falls downward in the raw material solution, thereby contacting the aqueous solution comprising the silver salt with the raw material solution, wherein, after said contacting. the aqueous solution comprising the silver salt exists in a form of a dispersed phase and the raw material solution comprising an alkyl ester of the polyunsaturated fatty acid exists in a form of a continuous phase; and
collecting the aqueous solution that has been contacted with the raw material solution,
wherein the temperature of the aqueous solution that is to be contacted with the raw material solution is from 5 to 30° C., and
the supply of the aqueous solution and the collection of the aqueous solution are carried out concurrently with each other.

11. The method according to claim 10, wherein
the contacting of the aqueous solution comprising the silver salt with the raw material solution comprising an alkyl ester of the polyunsaturated fatty acid comprises supplying the aqueous solution from an upper part of a first reaction vessel and supplying the raw material solution from a lower part of the first reaction vessel while flowing countercurrently to each other in the first reaction vessel to contact the aqueous solution and the raw material solution with each other, and
the collection of the aqueous solution comprises collecting the aqueous solution that has been contacted with the raw material solution from a part located below an inlet port for the raw material solution in the first reaction vessel.

12. The method according to claim 10, further comprising:
supplying the collected aqueous solution into an organic solvent such that the aqueous solution falls downward in the organic solvent, thereby contacting the aqueous solution with the organic solvent; and
collecting the organic solvent that has been contacted with the aqueous solution,
wherein the temperature of the aqueous solution to be contacted with the organic solvent is from 30 to 80° C., and
the supply of the aqueous solution and the collection of the organic solvent are carried out concurrently with each other.

13. The method according to claim 12, wherein
the contacting of the aqueous solution with the organic solvent comprises supplying the collected aqueous solution from an upper part of a second reaction vessel and supplying the organic solvent from a lower part of the second reaction vessel while flowing countercurrently to each other in the second reaction vessel to contact the aqueous solution and the organic solvent with each other, and
the collection of the organic solvent comprises collecting the organic solvent that has been contacted with the aqueous solution from a part located above an inlet port for the aqueous solution in the second reaction vessel.

14. The method according to claim 12, further comprising collecting the aqueous solution that has been contacted with the organic solvent.

15. The method according to claim 13, further comprising collecting the aqueous solution that has been contacted with the organic solvent from a part located below an inlet port for the organic solvent in the second reaction vessel.

16. The method according to claim 14, wherein the aqueous solution comprising a silver salt which is to be supplied into the raw material solution comprising an alkyl ester of the polyunsaturated fatty acid comprises the aqueous solution that has been collected after contacting the aqueous solution with the organic solvent.

17. The method according to claim 15, wherein the aqueous solution to be supplied into the first reaction vessel comprises the aqueous solution collected from the second reaction vessel.

18. The method according to claim 11, wherein the first reaction vessel is a closed system.

19. The method according to claim 13, wherein the second reaction vessel is a closed system.

20. The method according to claim 12, wherein the aqueous solution forms a dispersed phase and the organic solvent forms a continuous phase.

21. The method according to claim 10, wherein the dispersed phase is in a form of liquid droplets or mists.

22. The method according to claim 10, wherein the polyunsaturated fatty acid comprises eicosapentaenoic acid or docosahexaenoic acid.

23. The method according to claim 10, wherein, in the aqueous solution comprising the silver salt, the concentration of the silver salt is 30% by mass or more.

24. The method according to claim 12, wherein the organic solvent is at least one organic solvent selected from the group consisting of hexane and cyclohexane.

25. An apparatus for producing a composition comprising a polyunsaturated fatty acid,
the apparatus comprising a first reaction vessel,
wherein the first reaction vessel comprises a raw material solution inlet port through which a raw material solution comprising an alkyl ester of the polyunsaturated fatty acid is to be supplied into the reaction vessel, an aqueous solution inlet port through which an aqueous solution comprising a silver salt is to be supplied into the reaction vessel, an aqueous solution collection port through which the aqueous solution that has been contacted with the raw material solution is to be collected, and a raw material solution collection port through which the raw material solution that has been contacted with the aqueous solution is to be collected,
the raw material solution inlet port is arranged at the lower part of the first reaction vessel and above the aqueous solution collection port,
the aqueous solution inlet port is arranged at the upper part of the first reaction vessel, above the raw material solution inlet port and below the raw material solution collection port,
the aqueous solution comprising the silver salt which has been supplied through the aqueous solution inlet port flows downward in the first reaction vessel and the raw material solution which has been supplied through the raw material solution inlet port flows upward in the first reaction vessel while flowing countercurrently to each other in the reaction vessel so that the aqueous solution and the raw material solution are contacted with each other, and the contacted aqueous solution is collected outside the reaction vessel through the aqueous solution collection port, and
wherein the first reaction vessel further comprises a liquid distributor for converting the aqueous solution to be supplied through the aqueous solution inlet port into a dispersed phase.

26. The apparatus according to claim 25,
further comprising a second reaction vessel,
wherein the second reaction vessel comprises an organic solvent inlet port through which an organic solvent is to be supplied into the reaction vessel, an aqueous solution inlet port through which the aqueous solution collected through the aqueous solution collection port in the first reaction vessel is to be supplied into the second reaction vessel, an aqueous solution collection port through which the aqueous solution that has been contacted with the organic solvent is to be collected, and an organic solvent collection port through which the organic solvent that has been contacted with the aqueous solution is to be collected,
the organic solvent inlet port is arranged at the lower part of the second reaction vessel and above the aqueous solution collection port,
the aqueous solution inlet port is arranged at the upper part of the second reaction vessel, above the organic solvent inlet port and below the organic solvent collection port, and
the aqueous solution supplied through the aqueous solution inlet port flows downward in the second reaction vessel and the organic solvent supplied through the organic solvent inlet port flows upward in the second reaction vessel while flowing countercurrently to each other in the second reaction vessel so that the aqueous solution and the organic solvent are contacted with each other, and the contacted aqueous solution is collected outside the second reaction vessel through the aqueous solution collection port.

27. The apparatus according to claim 26, wherein the aqueous solution collected from the second reaction vessel is supplied into the first reaction vessel through the aqueous solution inlet port in the first reaction vessel.

28. The apparatus according to claim 26, wherein the first or second reaction vessel comprises a temperature controller for controlling the temperature of the aqueous solution in the reaction vessel.

29. The method according to claims claim 10, wherein the method is carried out using an apparatus comprising a first reaction vessel,
wherein the first reaction vessel comprises a raw material solution inlet port through which a raw material solution comprising an alkyl ester of the polyunsaturated fatty acid is to be supplied into the reaction vessel, an aqueous solution inlet port through which an aqueous solution comprising a silver salt is to be supplied into the reaction vessel, an aqueous solution collection port through which the aqueous solution that has been contacted with the raw material solution is to be collected, and a raw material solution collection port through which the raw material solution that has been contacted with the aqueous solution is to be collected,
the raw material solution inlet port is arranged at the lower part of the first reaction vessel and above the aqueous solution collection port,
the aqueous solution inlet port is arranged at the upper part of the first reaction vessel, above the raw material solution inlet port and below the raw material solution collection port,
the aqueous solution comprising the silver salt which has been supplied through the aqueous solution inlet port flows downward in the first reaction vessel and the raw material solution which has been supplied through the raw material solution inlet port flows upward in the first reaction vessel while flowing countercurrently to each other in the reaction vessel so that the aqueous solution and the raw material solution are contacted with each other, and the contacted aqueous solution is collected outside the reaction vessel through the aqueous solution collection port, and
wherein the first reaction vessel further comprises a liquid distributor for converting the aqueous solution to be supplied through the aqueous solution inlet port into a dispersed phase.

* * * * *